United States Patent
Hayes et al.

(10) Patent No.: US 9,737,485 B2
(45) Date of Patent: Aug. 22, 2017

(54) REMOTE LOADING OF SPARINGLY WATER-SOLUBLE DRUGS INTO LIPOSOMES

(71) Applicant: ZONEONE PHARMA, INC., San Francisco, CA (US)

(72) Inventors: Mark E. Hayes, San Francisco, CA (US); Charles O. Noble, San Francisco, CA (US); Francis C. Szoka, Jr., San Francisco (CA)

(73) Assignee: ZONEONE PHARMA, INC., San Francisco, CA (US)

( * ) Notice: Subject to any disclaimer, the term of this patent is extended or adjusted under 35 U.S.C. 154(b) by 0 days.

(21) Appl. No.: 15/216,416

(22) Filed: Jul. 21, 2016

(65) Prior Publication Data
US 2016/0324780 A1 Nov. 10, 2016

Related U.S. Application Data

(63) Continuation of application No. 14/171,654, filed on Feb. 3, 2014, now abandoned.
(Continued)

(51) Int. Cl.
*A61K 9/127* (2006.01)
*A61K 31/4196* (2006.01)
(Continued)

(52) U.S. Cl.
CPC .......... *A61K 9/1278* (2013.01); *A61K 9/1271* (2013.01); *A61K 9/1275* (2013.01);
(Continued)

(58) Field of Classification Search
CPC ..................................................... A61K 9/127
See application file for complete search history.

(56) References Cited

U.S. PATENT DOCUMENTS 3,932,657 A 1/1976 Rahman
4,016,290 A 4/1977 Rahman
(Continued)

FOREIGN PATENT DOCUMENTS

EP  2415470 A1  2/2012
WO  WO 00/09089 A1  2/2000
(Continued)

OTHER PUBLICATIONS

Anderson, B. et al., "Enhanced active liposomal loading of a poorly soluble ionizable drug using supersaturated drug solutions." *Journal of Controlled Release*, 162, pp. 330-339 (2012).
(Continued)

*Primary Examiner* — Gollamudi Kishore
(74) *Attorney, Agent, or Firm* — Morgan, Lewis & Bockius LLP; Jeffrey S. Mann

(57) ABSTRACT

The present invention provides liposome compositions containing sparingly soluble drugs that are used to treat life-threatening diseases. A preferred method of encapsulating a drug inside a liposome is by remote or active loading. Remote loading of a drug into liposomes containing a transmembrane electrochemical gradient is initiated by co-mixing a liposome suspension with a solution of drug, whereby the neutral form of the compound freely enters the liposome and becomes electrostatically charged thereby preventing the reverse transfer out of the liposome. There is a continuous build-up of compound within the liposome interior until the electrochemical gradient is dissipated or all the drug is encapsulated in the liposome. However, this process as described in the literature has been limited to drugs that are freely soluble in aqueous solution or solubilized as a water-soluble complex. This invention describes compositions and methods for remote loading drugs with low water solubility (<2 mg/mL). In the preferred embodi-
(Continued)

ment the drug in the solubilizing agent is mixed with the liposomes in aqueous suspension so that the concentration of solubilizing agent is lowered to below its capacity to completely solubilize the drug. This results in the drug precipitating but remote loading capability is retained. The process is scalable and, in liposomes in which the lipid composition and remote loading agent are optimized, the resulting drug-loaded liposomes are characterized by a high drug-to-lipid ratios and prolonged drug retention when the liposome encapsulated drug is administered to a subject.

17 Claims, 18 Drawing Sheets

Related U.S. Application Data

(60) Provisional application No. 61/759,914, filed on Feb. 1, 2013.

(51) Int. Cl.
| | | |
|---|---|---|
| *A61K 31/496* | (2006.01) | |
| *A61K 38/07* | (2006.01) | |
| *A61K 31/5377* | (2006.01) | |
| *A61K 9/00* | (2006.01) | |
| *A61K 9/19* | (2006.01) | |

(52) U.S. Cl.
CPC ........ *A61K 31/4196* (2013.01); *A61K 31/496* (2013.01); *A61K 31/5377* (2013.01); *A61K 38/07* (2013.01); *A61K 9/0019* (2013.01); *A61K 9/19* (2013.01)

(56) References Cited

U.S. PATENT DOCUMENTS

| | | | |
|---|---|---|---|
| 4,310,506 | A | 1/1982 | Baldeschwieler et al. |
| 4,397,867 | A | 8/1983 | Blake |
| 5,043,166 | A | 8/1991 | Barenholz |
| 5,192,549 | A | 3/1993 | Barenholz et al. |
| 5,316,771 | A | 5/1994 | Barenholz et al. |
| 5,616,341 | A | 4/1997 | Mayer et al. |
| 5,756,069 | A | 5/1998 | Torchilin et al. |
| 5,800,833 | A | 9/1998 | Hope et al. |
| 5,827,532 | A | 10/1998 | Mehlhorn |
| 5,837,282 | A | 11/1998 | Fenske et al. |
| 5,939,096 | A | 8/1999 | Clerc et al. |
| 8,029,795 | B2 | 10/2011 | Gwathmey |
| 8,329,213 | B2 | 12/2012 | Hong et al. |
| 8,591,942 | B2 * | 11/2013 | Javeri .................. A61K 9/1278 264/4.1 |
| 8,871,253 | B2 | 10/2014 | Li et al. |
| 2001/0006643 | A1 | 7/2001 | Hope |
| 2001/0033860 | A1 | 10/2001 | Gwathmey |
| 2002/0102293 | A1 | 8/2002 | Sachse et al. |
| 2004/0126886 | A1 | 7/2004 | Kan et al. |
| 2005/0175684 | A1 | 8/2005 | Gwathmey |
| 2005/0208119 | A1 | 9/2005 | Takemoto |
| 2006/0039965 | A1 | 2/2006 | Boch et al. |
| 2007/0014845 | A1 | 1/2007 | Zhang et al. |
| 2007/0110798 | A1 | 5/2007 | Drummond et al. |
| 2007/0116753 | A1 | 5/2007 | Hong et al. |
| 2008/0107747 | A1 | 5/2008 | Roederer |
| 2008/0213353 | A1 | 9/2008 | Barenholz et al. |
| 2009/0028931 | A1 | 1/2009 | Wasan et al. |
| 2009/0092661 | A1 | 4/2009 | Huang et al. |
| 2009/0196918 | A1 | 8/2009 | Joguparthi et al. |
| 2010/0311731 | A1 | 12/2010 | King, Jr. |
| 2011/0178287 | A1 | 7/2011 | Glucksmann et al. |
| 2012/0021042 | A1 | 1/2012 | Panzner et al. |

FOREIGN PATENT DOCUMENTS

| | | | |
|---|---|---|---|
| WO | WO 2011/092708 | | 8/2011 |
| WO | 2012/118376 | * | 9/2012 |
| WO | WO 2012/118376 A1 | | 9/2012 |
| WO | WO 2014/153192 | | 9/2014 |

OTHER PUBLICATIONS

Berge, S. et al., "Pharmaceutical Salts." *Journal of Pharmaceutical Science*, 66, pp. 1-19 (1977).
Challa, R. et al., "Cyclodextrins in Drug Delivery: An Updated Review." *AAPS PharmSciTech*, 6(2), pp. E329-E357 (2005).
Drummond D. et al., "Pharmacokinetics and in vivo drug release rates in liposomal nanocarrier development." *J. Pharm.Sci.*, 97(11), pp. 4696-4740 (2008).
Li, C. et al., "Novel sulfobutyl ether cyclodextrin gradient leads to highly active liposomal irinotecan formulation." *Journal of Pharmacy and Pharmacology*, 63, pp. 765-773 (2011).
Loftsson, T. and Brewster, M., "Pharmaceutical applications of cyclodextrins: basic science and product development." *Journal of Pharmacy and Pharmacology*, 62, pp. 1607-1621 (2010).
Zucker, D. et al., "Liposome drugs' loading efficiency: a working model based on loading conditions and drug's physicochemical properties." *Journal of Controlled Release*, 139, pp. 73-80 (2009).
Brittenham, G. "Iron-Chelating Therapy for transfusional Iron Overload", *N Engl J Med* 364:146-56 (2011).
Cullis et al., "Influence of pH gradients on the transbilayer transport of drugs, lipids, peptides and metal ions into large unilamellar vesicles", *Biochimica et Biophysica Acta*, 1331 187-211 (1997).
Fleming et al., "Iron overload in human disease". *N Engl J Med.* 366(4):348-59 (2012).
Guilmette et al., "Pharmacokinetics of the iron chelating agent desferrioxamine as affected by liposome encapsulation: potential in treatment of chronic hemosiderosis". *Life Sci*. 22(4):313-2 (1978).
Ihnat et al., "Synthesis and solution properties of deferoxamine amides", *J Pharm Sci.* 89(12):1525-36 (2000).
Lau et al., "Liposome-encapsulated desferrioxamine in experimental iron overload". *Br J Haematol.* 47(4):505-18 (1981).
Postma et al., "Absorption and biodistribution of 111indium-labelled desferrioxamine (111In-DFO) after subcutaneous injection of 111In-DFO liposomes". *J Control Release.* 58(1):51-60 (1999).
Rahman et al., "Intracellular plutonium removal by liposome-encapsulated chelating agent". *Science* (Wash. D.C.) 180:300-302 (1973).
Weinberg et al., "Iron withholding: a defense against disease". *J Alzheimers Dis*. 13(4):451-63 (2008).
Young et al., "Liposome entrapped desferrioxamine and iron transporting ionophores: a new approach to iron chelation therapy". *Br J Haematol.* 41(3):357-63 (1979).
Fritze et al., "Remote loading of doxorubicin into liposomes driven by a transmembrane phosphate gradient." *Biochimica et Biophysica Acta* 1758, 1633-1640 (2006).
Liu et al., "A Versatile Prodrug Approach for Liposomal Core-Loading of Water-Insoluble Camptothecin Anticancer Drugs." *Journal of the American Chemical Society*, vol. 124, No. 6 (2002).

* cited by examiner

Liposome Classification

- Multilamellar vesicles (MLV)
  - Multiple bilayers surrounding aqueous core
- Unilamellar vesicles
  - Single bilayer surrounding aqueous core
  - Small unilamellar vesicles (SUVs)
    - Diameter < 60 nm
  - Large unilamellar vesicles (LUVs)
    - Diameter > 80 nm

REMOTE LOADING OF SPARINGLY WATER-SOLUBLE DRUGS INTO LIPOSOMES

CROSS REFERENCE TO RELATED APPLICATIONS

This application is a Continuation of U.S. application Ser. No. 14/171,654 filed Feb. 3, 2014 which claims benefit of U.S. Provisional Patent Application No. 61/759,914 filed Feb. 1, 2013, all of which are incorporated herein by reference in their entireties.

BACKGROUND OF THE INVENTION

This invention relates to the fields of pharmaceutical compositions, methods for making them and the uses of the resulting compositions in drug therapy. The pharmaceutical compositions include the active therapeutic agent encapsulated within the aqueous interior of a liposome vesicle.

DESCRIPTION OF THE RELATED ART

The pharmaceutical industry, in its quest for improved drugs, has generated a large number of potent compounds that are sparingly soluble in water, the ubiquitous solvent that makes life possible. The low water solubility of these new drugs has made it difficult to deliver them in animals including humans. This has created the need for drug delivery systems that can solubilize sparingly water-soluble drugs to enable to their delivery in the body.

Liposomes are vesicle structures usually composed of a bilayer membrane of amphipathic molecules such as, phospholipids, entrapping an aqueous core. The diameters and morphology of various types of liposomes are illustrated in FIG. 1. Drugs are either encapsulated in the aqueous core or interdigitated in the bilayer membrane. Drugs interdigitated in the membrane transfer out of the liposome when it is diluted into the body. Importantly, drugs that are encapsulated in the aqueous core or held in complexes in the aqueous core are retained substantially longer than drugs in the bilayer. The use of liposomes with drugs encapsulated in the aqueous core for drug delivery is well established (D. Drummond et al., *J. Pharm. Sci.*, (2008) 97(11):4696-4740, PMID 10581328).

A variety of loading methods for encapsulating functional compounds, particularly drugs, in liposomes is available. Hydrophilic compounds for example can be encapsulated in liposomes by hydrating a mixture of the functional compounds and vesicle-forming lipids. This technique is called passive loading. The functional compound is encapsulated in the liposome as the nanoparticle is formed. The available lipid vesicle (liposome) production procedures are satisfactory for most applications where water-soluble drugs are encapsulated (G. Gregoriadis, Ed., *Liposome Technology*, (2006) Liposome Preparation and Related Techniques, 3rd Ed.) However, the manufacture of lipid vesicles that encapsulate drugs sparing water-soluble (e.g., with a water solubility less than 2 mg/mL) in the aqueous inner compartment of the liposome is exceedingly difficult (D. Zucker et al., *Journal of Controlled Release* (2009) 139:73-80, PMID 19508880).

Passive loading of lipophilic and to a lesser extent amphiphilic functional compounds is somewhat more efficient than hydrophilic functional compounds because they partition in both the lipid bilayer and the intraliposomal (internal) aqueous medium. However, using passive loading, the final functional-compound-to-lipid ratio as well as the encapsulation efficiency are generally low. The concentration of drug in the liposome equals that of the surrounding fluid and drug not entrapped in the internal aqueous medium is washed away after encapsulation. Moreover drugs loaded into the bilayer are released from the liposome very rapidly when the liposome is injected into a subject. For sustained release of the drug in a patient it is preferable that the drug is encapsulated within the interior of the lipsosome.

Certain hydrophilic or amphiphilic compounds can be loaded into preformed liposomes using transmembrane pH- or ion-gradients (D. Zucker et al., *Journal of Controlled Release* (2009) 139:73-80). This technique is called active or remote loading. Compounds amenable to active loading should be able to change from an uncharged form, which can diffuse across the liposomal membrane, to a charged form that is not capable thereof. Typically, the functional compound is loaded by adding it to a suspension of liposomes prepared to have a lower inside/higher outside pH- or ion-gradient. Via active loading, a high functional-compound-to-lipid mass ratio and a high loading efficiency (up to 100%) can be achieved. Examples are active loading of anticancer drugs doxorubicin, daunorubicin, and vincristine (P. R. Cullis et al., *Biochimica et Biophysica Acta*, (1997) 1331:187-211, and references therein).

Hydrophobic drugs are only considered capable of loading into liposomes through membrane intercalation via some passive loading/assembly mechanism. Wasan et al. states "Agents that have hydrophobic attributes can intercalate into the lipid bilayer and this can be achieved by adding the agent to the preformed liposomes." in a description of the use of micelles to transfer sparingly soluble agents to a liposome bilayer (US 2009/0028931).

Remote loading of a sparingly soluble drug into a liposome under conditions where the drug is above its solubility limit and is in the form of a precipitate is an unexpected event. D. Zucker et al., *Journal of Controlled Release* (2009) 139:73-80 states "Hydrophobic molecules may aggregate, and these aggregates have low permeability across the liposomal membrane. Thus, when the non-polar/polar surface area ratio is >2.31 (see FIG. 4 in Zucker et al. *Journal of Controlled Release* (2009) 139:73-80), it is necessary that the drug would have a reasonable solubility, >1.9 mM, in order to achieve high loading because only soluble uncharged molecules can enter the liposome." (D. Zucker et al., *Journal of Controlled Release* (2009) 139:73-80).

To date, a method has not been developed for the active loading of the aqueous core of a liposome with a sparingly water-soluble agent from a precipitate.

SUMMARY OF THE INVENTION

Figure 1:
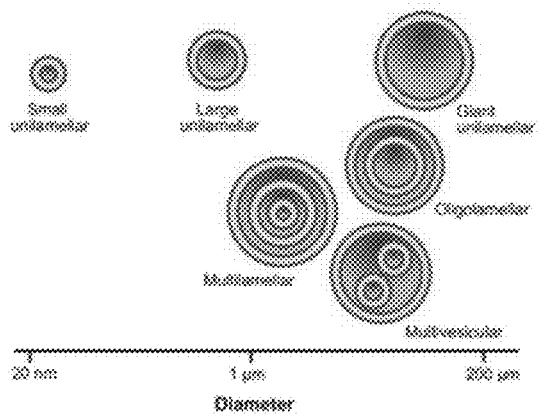
FIG. 1 illustrates the diameters and morphology of various types of liposomes.

In utilizing liposomes for delivery of functional compounds, it is generally desirable to load the liposomes to high concentration, resulting in a high functional-compound-lipid mass ratio, since this reduces the amount of liposomes to be administered per treatment to attain the required therapeutic effect, all the more since several lipids used in liposomes have a dose-limiting toxicity by themselves. The loading percentage is also of importance for cost efficiency, since poor loading results in a great loss of the active compound.

In an exemplary embodiment, the invention provides a liposome comprising a liposomal lipid membrane encapsulating an internal aqueous medium. The internal aqueous medium comprises an aqueous solution of a complex between a trapping agent and a sparingly water-soluble therapeutic agent.

In a further exemplary embodiment, the invention provides pharmaceutical formulations comprising a liposome of the invention. The formulations include the liposome and a pharmaceutically acceptable diluent or excipient. In various embodiments, the pharmaceutical formulation is in a unit dosage format, providing a unit dosage of the therapeutic agent encapsulated in the liposome.

In another exemplary embodiment, the invention provides methods of making the liposomes of the invention. In various embodiments, there is provided a method of remotely loading a liposome with an agent that is sparingly water-soluble. The method comprises: a) incubating an aqueous mixture comprising: (i) a liposome suspension having a proton and/or ion gradient that exists across the liposomal membrane; (ii) with an aqueous suspension of a sparingly soluble drug (iii) wherein the drug suspension is made by completely dissolving the drug in an aprotic solvent or polyol and diluting it into the aqueous solution beyond the point of drug solubility where a precipitate is formed, wherein incubating the combined liposome drug precipitate mixture for a period of time results in the drug accumulating within the liposome interior in response to the proton/ion gradient. The mixture used to load the liposome with the agent is prepared such that a proton- and/or ion-gradient exists across the liposomal membrane between the internal aqueous membrane and the external aqueous medium. The incubating can be for any useful period but is preferably for a period of time sufficient to cause at least part of the insoluble drug precipitate to accumulate in the internal aqueous medium under the influence of the proton and/or ion gradient.

Other embodiments, objects and advantages are set forth in the Detailed Description that follows.

DESCRIPTION OF THE PREFERRED EMBODIMENTS

Introduction

In utilizing liposomes for delivery of functional compounds, it is generally desirable to load the liposomes to high concentration, resulting in a high agent-lipid mass ratio, since this reduces the amount of liposomes to be administered per treatment to attain the required therapeutic effect of the agent, all the more since several lipids used in liposomes have a dose-limiting toxicity by themselves. The loading percentage is also of importance for cost efficiency, since poor loading results in an increase loss of agent during the loading of the agent into the liposome.

The present invention provides liposomes encapsulating agents, e.g., sparingly water-soluble, methods of making such liposomes, formulations containing such liposomes and methods of making the liposomes and formulations of the invention.

In an exemplary embodiment, the invention provides a liposome having a membrane encapsulating an aqueous compartment. The liposome is prepared such that a proton- and/or ion-gradient exists across the liposomal membrane between the internal aqueous compartment and the external aqueous medium. The agent is dissolved in an aprotic solvent at a concentration that when diluted in the liposome suspension to form the remote loading mixture its solubility in the suspension is exceeded and the agent forms a precipitate. A portion of the agent precipitate is loaded into the liposome aqueous compartment using a proton- and/or ion-gradient across the liposomal membrane between the internal aqueous compartment and the external aqueous medium.

In some embodiments, essentially the entire amount of the insoluble agent precipitate in the remote loading mixture is loaded into the aqueous compartment of the liposome. In an exemplary embodiment, at least about 95%, at least about 90%, at least about 85%, at least about 80% or at least about 70% of the insoluble drug precipitate in the remote loading mixture is loaded into the aqueous compartment of the liposome.

Liposomes

The term liposome is used herein in accordance with its usual meaning, referring to microscopic lipid vesicles composed of a bilayer of phospholipids or any similar amphipathic lipids encapsulating an internal aqueous medium. The liposomes of the present invention can be unilamellar vesicles such as small unilamellar vesicles (SUVs) and large unilamellar vesicles (LUVs), and multilamellar vesicles (MLV), typically varying in size from 30 nm to 200 nm. No particular limitation is imposed on the liposomal membrane structure in the present invention. The term liposomal membrane refers to the bilayer of phospholipids separating the internal aqueous medium from the external aqueous medium.

Exemplary liposomal membranes useful in the current invention may be formed from a variety of vesicle-forming lipids, typically including dialiphatic chain lipids, such as phospholipids, diglycerides, dialiphatic glycolipids, single lipids such as sphingomyelin and glycosphingolipid, cholesterol and derivates thereof, and combinations thereof. As defined herein, phospholipids are amphiphilic agents having hydrophobic groups formed of long-chain alkyl chains, and a hydrophilic group containing a phosphate moiety. The group of phospholipids includes phosphatidic acid, phosphatidyl glycerols, phosphatidylcholines, phosphatidylethanolamines, phosphatidylinositols, phosphatidylserines, and mixtures thereof. Preferably, the phospholipids are chosen from 1,2-dipalmitoyl-sn-glycero-3-phosphocholine (DPPC), dimyristoyl-phosphatidylcholine (DMPC), hydrogenated soy phosphatidylcholine (HSPC), soy phosphatidylcholine (SPC), dimyristoylphosphatidylglycerol (DMPG), disrearoylphosphatidylglycerol (DSPG), 1-palmitoyl-2-oleoyl-sn-glycero-3-phosphocholine (POPC), 1,2-dioleoyl-sn-glycero-3-phosphocholine (DOPC) distearoyl phosphatidylcholine (DSPC), egg yolk phosphatidylcholine (EYPC) or hydrogenated egg yolk phosphatidylcholine (HEPC), sterol modified lipids (SML), cationic lipids and inverse-zwitterlipids.

Liposomal membranes according to the present invention may further comprise ionophores like nigericin and A23187.

In the method according to the present invention, an exemplary liposomal phase transition temperature is between −25° C. and 100° C., e.g., between 4° C. and 65° C. The phase transition temperature is the temperature required to induce a change in the physical state of the lipids constituting the liposome, from the ordered gel phase, where the hydrocarbon chains are fully extended and closely packed, to the disordered liquid crystalline phase, where the hydrocarbon chains are randomly oriented and fluid. Above the phase transition temperature of the liposome, the permeability of the liposomal membrane increases. Choosing a high transition temperature, where the liposome would always be in the gel state, could provide a non-leaking liposomal composition, i.e. the concentration of the sparingly water-soluble agent in the internal aqueous medium is maintained during exposure to the environment. Alternatively, a liposome with a transition temperature between the starting and ending temperature of the environment it is exposed to provides a means to release the sparingly water-soluble agent when the liposome passes through its transition temperature. Thus, the process temperature for the active-loading technique typically is above the liposomal phase transition temperature to facilitate the active-loading process. As is generally known in the art, phase transition temperatures of liposomes can, among other parameters, be influenced by the choice of phospholipids and by the addition of steroids like cholesterol, lanosterol, cholestanol, stigmasterol, ergosterol, and the like. Hence, in an embodiment of the invention, a method according to any of the foregoing is provided in which the liposomes comprise one or more components selected from different phospholipids and cholesterol in several molar ratios in order to modify the transition, the required process temperature and the liposome stability in plasma. Less cholesterol in the mixture will result in less stable liposomes in plasma. An exemplary phospholipid composition of use in the invention comprises between about 10 and about 50 mol % of steroids, preferably cholesterol.

In accordance with the invention, liposomes can be prepared by any of the techniques now known or subsequently developed for preparing liposomes. For example, the liposomes can be formed by the conventional technique for preparing multilamellar lipid vesicles (MLVs), that is, by depositing one or more selected lipids on the inside walls of a suitable vessel by dissolving the lipids in chloroform and then evaporating the chloroform, and by then adding the aqueous solution which is to be encapsulated to the vessel, allowing the aqueous solution to hydrate the lipid, and swirling or vortexing the resulting lipid suspension. This process engenders a mixture including the desired liposomes. Alternatively, techniques used for producing large unilamellar lipid vesicles (LUVs), such as reverse-phase evaporation, infusion procedures, and detergent dilution, can be used to produce the liposomes. A review of these and other methods for producing lipid vesicles can be found in the text Liposome Technology, Volume I, Gregory Gregoriadis Ed., CRC Press, Boca Raton, Fla., (1984), which is incorporated herein by reference. For example, the lipid-containing particles can be in the form of steroidal lipid vesicles, stable plurilamellar lipid vesicles (SPLVs), monophasic vesicles (MPVs), or lipid matrix carriers (LMCs). In the case of MLVs, if desired, the liposomes can be subjected to multiple (five or more) freeze-thaw cycles to enhance their trapped volumes and trapping efficiencies and to provide a more uniform interlamellar distribution of solute.

Following liposome preparation, the liposomes are optionally sized to achieve a desired size range and relatively narrow distribution of liposome sizes. A size range of about 20-200 nanometers allows the liposome suspension to be sterilized by filtration through a conventional filter, typically a 0.22 or 0.4 micron filter. The filter sterilization method can be carried out on a high through-put basis if the liposomes have been sized down to about 20-200 nanometers. Several techniques are available for sizing liposomes to a desired size. Sonicating a liposome suspension either by bath or probe sonication produces a progressive size reduction down to small unilamellar vesicles less than about 50 nanometer in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 50 and 500 nanometers, are observed. In both methods, the particle size distribution can be monitored by conventional laser-beam particle size determination. Extrusion of liposome through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve a gradual reduction in liposome size. Alternatively controlled size liposomes can be prepared using microfluidic techniques wherein the lipid in an organic solvent such as ethanol or ethanol-aprotic solvent mixtures is rapidly mixed with the aqueous medium, so that the organic solvent/water ratio is less than 30%, in a microchannel with dimensions less than 300 microns and preferable less than 150 microns in wide and 50 microns in height. The organic solvent is then removed from the liposomes by dialysis. Other useful sizing methods such as sonication, solvent vaporization or reverse phase evaporation are known to those of skill in the art.

Exemplary liposomes for use in various embodiments of the invention have a size of from about 30 nanometers to about 40 microns.

The internal aqueous medium, as referred to herein, typically is the original medium in which the liposomes were prepared and which initially becomes encapsulated upon formation of the liposome. In accordance with the present invention, freshly prepared liposomes encapsulating the original aqueous medium can be used directly for active loading. Embodiments are also envisaged however wherein the liposomes, after preparation, are dehydrated, e.g. for storage. In such embodiments the present process may involve addition of the dehydrated liposomes directly to the external aqueous medium used to create the transmembrane gradients. However it is also possible to hydrate the liposomes in another external medium first, as will be understood by those skilled in the art. Liposomes are optionally dehydrated under reduced pressure using standard freeze-drying equipment or equivalent apparatus. In various embodiments, the liposomes and their surrounding medium are frozen in liquid nitrogen before being dehydrated and placed under reduced pressure. To ensure that the liposomes will survive the dehydration process without losing a substantial portion of their internal contents, one or more protective sugars are typically employed to interact with the lipid vesicle membranes and keep them intact as the water in the system is removed. A variety of sugars can be used, including such sugars as trehalose, maltose, sucrose, glucose, lactose, and dextran. In general, disaccharide sugars have been found to work better than monosaccharide sugars, with the disaccharide sugars trehalose and sucrose being most effective. Other more complicated sugars can also be used. For example, aminoglycosides, including streptomycin and dihydrostreptomycin, have been found to protect liposomes during dehydration. Typically, one or more sugars are included as part of either the internal or external media of the lipid vesicles. Most preferably, the sugars are included in both the internal and external media so that they can interact with both the inside and outside surfaces of the liposomes' membranes. Inclusion in the internal medium is accomplished by adding the sugar or sugars to the buffer which becomes encapsulated in the lipid vesicles during the liposome formation process. In these embodiments the external medium used during the active loading process should also preferably include one or more of the protective sugars As is generally known to those skilled in the art, polyethylene glycol (PEG)-lipid conjugates have been used extensively to improve circulation times for liposome-encapsulated functional compounds, to avoid or reduce premature leakage of the functional compound from the liposomal composition and to avoid detection of liposomes by the body's immune system. Attachment of PEG-derived lipids onto liposomes is called PEGylation. Hence, in an exemplary embodiment of the invention, the liposomes are PEGylated liposomes. PEGylation can be accomplished by incubating a reactive derivative of PEG with the target liposomes. Suitable PEG-derived lipids according to the invention, include conjugates of DSPE-PEG, functionalized with one of carboxylic acids, glutathione (GSH), maleimides (MAL), 3-(2-pyridyldithio) propionic acid (PDP), cyanur, azides, amines, biotin or folate, in which the molecular weight of PEG is between 2000 and 5000 g/mol. Other suitable PEG-derived lipids are mPEGs conjugated with ceramide, having either $C_8$- or $C_{16}$-tails, in which the molecular weight of mPEG is between 750 and 5000 daltons. Still other appropriate ligands are mPEGs or functionalized PEGs conjugated with glycerophospholipds like 1,2-dimyristoyl-sn-glycero-3-phosphoethanolamine (DMPE), 1,2-dipalmitoyl-sn-glycero-3-phosphoethanolamine (DPPE), 1,2-dioleoyl-sn-glycero-3-phosphoethanolamine (DOPE) and 1,2-distearoyl-sn-glycero-3-phosphoethanolamine (DSPE), and the like. PEGylation of liposomes is a technique generally known by those skilled in the art.

In various embodiments, the liposomes are PEGylated with DSPE-PEG-GSH conjugates (up to 5 mol %) and/or DSPE-mPEG conjugates (wherein the molecular weight of PEG is typically within the range of 750-5000 daltons, e.g. 2000 daltons). The phospholipid composition of an exemplary PEGylated lipsome of the invention may comprise up to 5-20 mol % of PEG-lipid conjugates.

Furthermore, in certain embodiments, one or more moieties that specifically target the liposome to a particular cell type, tissue or the like are incorporated into the membrane. Targeting of liposomes using a variety of targeting moieties (e.g., ligands, receptors and monoclonal antibodies) has been previously described. Suitable examples of such targeting moieties include hyaluronic acid, anti-ErbB family antibodies and antibody fragments, lipoprotein lipase (LPL), [α]2-macroglobulin ([α]2M), receptor associated protein (RAP), lactoferrin, desmoteplase, tissue- and urokinase-type plasminogen activator (tPA/uPA), plasminogen activator inhibitor (PAI-I), tPA/uPA:PAI-1 complexes, melanotransferrin (or P97), thrombospondin 1 and 2, hepatic lipase, factor Vila/tissue-factor pathway inhibitor (TFPI), factor Villa, factor IXa, A[β]1-40, amyloid-[β] precursor protein (APP), CI inhibitor, complement C3, apolipoproteinE (apoE), pseudomonas exotoxin A, CRM66, HIV-I Tat protein, rhinovirus, matrix metalloproteinase 9 (MMP-9), MMP-13 (collagenase-3), spingolipid activator protein (SAP), pregnancy zone protein, antithrombin III, heparin cofactor II, [α]1-antitrypsin, heat shock protein 96 (HSP-96), platelet-derived growth factor (PDGF), apolipoproteinJ (apoJ, or clusterin), A[β] bound to apoJ and apoE, aprotinin, angiopep-2 (TFFYGGSRGKRNNFKTEEY), very-low-density lipoprotein (VLDL), transferrin, insulin, leptin, an insulin-like growth factor, epidermal growth factors, lectins, peptidomimetic and/or humanized monoclonal antibodies, dingle chain antibodies or peptides specific for said receptors (e.g., sequences HAIYPRH and THRPPMWSPVWP that bind to the human transferrin receptor, or anti-human transferrin receptor (TfR) monoclonal antibody A24), hemoglobin, non-toxic portion of a diphtheria toxin polypeptide chain, all or a portion of the diphtheria toxin B chain, all or a portion of a non-toxic mutant of diphtheria toxin CRM197, apolipoprotein B, apolipoprotein E (e.g., after binding to polysorb-80 coating), vitamin D-binding protein, vitamin A/retinol-binding protein, vitamin B12/cobalamin plasma carrier protein, glutathione and transcobalamin-B 12.

Targeting mechanisms generally require that the targeting agents be positioned on the surface of the liposome in such a manner that the target moieties are available for interaction with the target, for example, a cell surface receptor. In an exemplary embodiment, the liposome is manufactured to include a connector portion incorporated into the membrane at the time of forming the membrane. An exemplary connector portion has a lipophilic portion which is firmly embedded and anchored in the membrane. An exemplary connector portion also includes a hydrophilic portion which is chemically available on the aqueous surface of the liposome. The hydrophilic portion is selected so that it will be chemically suitable to form a stable chemical bond with the targeting agent, which is added later. Techniques for incorporating a targeting moiety in the liposomal membrane are generally known in the art.

In an exemplary embodiment, the liposome includes HSPC, cholesterol, PEG-DSPE and a combination thereof. In an exemplary embodiment, the liposome includes from about 50 mol to about 70 mol HSPC, from about 30 mol to about 50 mol cholesterol and from about 1 mol to about 10 mol PEG-DSPE. In one embodiment, the liposome includes about 60 mol HSPC, about 40 mol cholesterol and about 5 mol PEG DSPE.

Sparingly Water-Soluble Agent

As indicated above, the present invention provides liposomes encapsulating a sparingly water-soluble agent. In the context of the present invention the term 'sparingly water-soluble' means being insoluble or having a very limited solubility in water, more in particular having an aqueous solubility of less than 2 mg/mL, e.g., less than 1.9 mg/mL, e.g., having an aqueous solubility of less than 1 mg/mL. As used herein, water solubilities refer to solubilities measured at ambient temperature, which is typically about 20° C. In an exemplary embodiment, the water solubility of the agent is measured at about pH=7.

According to an exemplary embodiment of the invention, the sparingly water-soluble agent is a therapeutic agent selected from the group of a therapeutic is selected from a group consisting of an anthracycline compound, a camptothecin compound, a vinca alkaloid, an ellipticine compound, a taxane compound, a wortmannin compound, a geldanamycin compound, a pyrazolopyrimidine compound, a peptide-based compound such as carfilzomib, a steroid compound, a derivative of any of the foregoing, a pro-drug of any of the foregoing, and an analog of any of the foregoing.

Exemplary small molecule compounds having a water solubility less than about 2 mg/mL include, but are not limited to, carfilzomib, voriconazole, amiodarone, ziprasidone, aripiprazole, imatinib, lapatinib, cyclopamine, oprozomib, CUR-61414, PF-05212384, PF-4691502, toceranib, PF-477736, PF-337210, sunitinib, SU14813, axitinib, AG014699, veliparib, MK-4827, ABT-263, SU11274, PHA665752, Crizotinib, XL880, PF-04217903, XR5000, AG14361, veliparib, bosutunib, PD-0332991, PF-01367338, AG14361, NVP-ADW742, NVP-AUY922, NVP-LAQ824, NVP-TAE684, NVP-LBH589, erubulin, doxorubicin, daunorubicin, mitomycin C, epirubicin, pirarubicin, rubidomycin, carcinomycin, N-acetyladriamycin, rubidazone, 5-imido daunomycin, N-acetyl daunomycin, daunory line, mitoxanthrone, camptothecin, 9-aminocamptothecin, 7-ethylcamptothecin, 7-Ethyl-10-hydroxy-camptothecin, 10-hydroxycamptothecin, 9-nitrocamptothecin, 1O,11-methylenedioxycamptothecin, 9-amino-1O,11-methylenedioxycamptothecin, 9-chloro-10,11-methylenedioxycamptothecin, irinotecan, lurtotecan, silatecan, (7-(4-methylpiperazinomethylene)-10,II-ethylenedioxy-20(S)-camptothecin, 7-(4-methylpiperazinomethylene)-10, II-methylenedioxy-20(S)-camptothecin, 7-(2-N-isopropylamino)ethyl)-(20S)-camptothecin, CKD-602, vincristine, vinblastine, vinorelbine, vinflunine, vinpocetine, vindesine, ellipticine, 6-3-aminopropyl-ellipticine, 2-diethylaminoethyl-ellipticinium, datelliptium, retelliptine, paclitaxel, docetaxel, diclofenac, bupivacaine, 17-Dimethylaminoethylamino-17-demethoxygeldanamycin, cetirizine, fexofenadine, primidone and other catecholamines, epinephrine, (S)-2-(2,4-dihydroxyphenyl)-4,5-dihydro-4-methyl-4-thiazolecarboxylic acid (deferitrin), (S)-4,5-dihydro-2-(3-hydroxy-2-pyridinyl)-4-methyl-4-thiazolecarboxylic acid (desferrithiocin), (S)-4,5-dihydro-2-[2-hydroxy-4-(3,6,9,12-tetraoxatridecyloxy)phenyl]-4-methyl-4-thiazolecarboxylic acid, (S)-4,5-dihydro-2-[2-hydroxy-4-(3,6-dioxaheptyloxy) phenyl]-4-methyl-4-thiazolecarboxylic acid, ethyl (S)-4,5-dihydro-2-[2-hydroxy-4-(3,6-dioxaheptyloxy)phenyl]-4-methyl-4-thiazolecarboxylate, (S)-4,5-dihydro-2-[2-hydroxy-3-(3,6,9-trioxadecyloxy)]-4-methyl-4-thiazolecarboxylic acid, desazadesferrithiocin salts, prodrugs and derivatives of these medicinal compounds and mixtures thereof.

An exemplary therapeutic agent is selected from: an antihistamine ethylenediamine derivative, bromphenifamine, diphenhydramine, an anti-protozoal drug, quinolone, iodoquinol, an amidine compound, pentamidine, an antihelmintic compound, pyrantel, an anti-schistosomal drug, oxaminiquine, an antifungal triazole derivative, fliconazole, itraconazole, ketoconazole, miconazole, an antimicrobial cephalosporin, chelating agents, deferoxamine, deferasirox, deferiprone, FBS0701, cefazolin, cefonicid, cefotaxime, ceftazimide, cefuoxime, an antimicrobial beta-lactam derivative, aztreopam, cefmetazole, cefoxitin, an antimicrobial of erythromycin group, erythromycin, azithromycin, clarithromycin, oleandomycin, a penicillin compound, benzylpenicillin, phenoxymethylpenicillin, cloxacillin, methicillin, nafcillin, oxacillin, carbenicillin, a tetracycline compound, novobiocin, spectinomycin, vancomycin; an antimycobacterial drug, aminosalicycic acid, capreomycin, ethambutol, isoniazid, pyrazinamide, rifabutin, rifampin, clofazimine, an antiviral adamantane compound, amantadine, rimantadine, a quinidine compound, quinine, quinacrine, chloroquine, hydroxychloroquine, primaquine, amodiaquine, mefloquine, an antimicrobial, qionolone, ciprofloxacin, enoxacin, lomefloxacin, nalidixic acid, norfloxacin, ofloxacin, a sulfonamide; a urinary tract antimicrobial, nitrofurantoin, trimetoprim; anitroimidazoles derivative, metronidazole, a cholinergic quaternary ammonium compound, ambethinium, neostigmine, physostigmine, an anti-Alzheimer aminoacridine, tacrine, an anti-parkinsonal drug, benztropine, biperiden, procyclidine, trihexylhenidyl, an anti-muscarinic agent, atropine, hyoscyamine, scopolamine, propantheline, an adrenergic compound, dopamine, serotonin, a hedgehog inhibitor, albuterol, dobutamine, ephedrine, epinephrine, norepinephrine, isoproterenol, metaproperenol, salmetrol, terbutaline, a serotonin reuptake inhibitor, an ergotamine derivative, a myorelaxant, a curare series, a central action myorelaxant, baclophen, cyclobenzepine, dentrolene, nicotine, a nicotine receptor antagonist, a beta-adrenoblocker, acebutil, amiodarone, abenzodiazepine compound, ditiazem, an antiarrhythmic drug, diisopyramide, encaidine, a local anesthetic compound, procaine, procainamide, lidocaine, flecaimide, quinidine, an ACE inhibitor, captopril, enelaprilat, Hsp90 inhibitor, fosinoprol, quinapril, ramipril; an opiate derivative, codeine, meperidine, methadone, morphine, an antilipidemic, fluvastatin, gemfibrosil, an HMG-coA inhibitor, pravastatin, a hypotensive drug, clonidine, guanabenz, prazocin, guanethidine, granadril, hydralazine, a non-coronary vasodilator, dipyridamole, an acetylcholine esterase inhibitor, pilocarpine, an alkaloid, physostigmine, neostigmine, a derivative of any of the foregoing, a pro-drug of any of the foregoing, and analog of any of the foregoing.

This list of agents, however, is not intended to limit the scope of the invention. In fact, the compound encapsulated within the liposome can be any sparingly water-soluble amphipathic weak base or amphipathic weak acid. As noted above, embodiments wherein the sparingly water-soluble agent is not a pharmaceutical or medicinal agent are also encompassed by the present invention.

Typically, within the context of the present invention, sparingly water-soluble amphipathic weak bases have an octanol-water distribution coefficient (log D) at pH 7 between −2.5 and 2 and pKa<11, while sparingly water-soluble amphipathic weak acids have a log D at pH 7 between −2.5 and 2 and pKa>3.

Typically, the terms weak base and weak acid, as used in the foregoing, respectively refer to compounds that are only partially protonated or deprotonated in water. Examples of protonable agents include compounds having an amino group, which can be protonated in acidic media, and compounds which are zwitterionic in neutral media and which can also be protonated in acidic environments. Examples of deprotonable agents include compounds having a carboxy group, which can be deprotonated in alkaline media, and compounds which are zwitterionic in neutral media and which can also be deprotonated in alkaline environments.

The term zwitterionic refers to compounds that can simultaneously carry a positive and a negative electrical charge on different atoms. The term amphipathic, as used in the foregoing is typically employed to refer to compounds having both lipophilic and hydrophilic moieties. The foregoing implies that aqueous solutions of compounds being weak amphipathic acids or bases simultaneously comprise charged and uncharged forms of said compounds. Only the uncharged forms may be able to cross the liposomal membrane.

When agents of use in the present invention contain relatively basic or acidic functionalities, salts of such compounds are included in the scope of the invention. Salts can be obtained by contacting the neutral form of such compounds with a sufficient amount of the desired acid or base, either neat or in a suitable inert solvent. Examples of salts for relative acidic compounds of the invention include sodium, potassium, calcium, ammonium, organic amino, or magnesium salts, or a similar salts. When compounds of the present invention contain relatively basic functionalities, acid addition salts can be obtained by contacting the neutral form of such compounds with a sufficient amount of the desired acid, either neat or in a suitable inert solvent. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science* 1977, 66: 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

An exemplary agent is a small organic molecule with a molecular weight between about 100 Da and 3000 Da.

In the embodiment in which a unit dosage format is formed, the liposome will, in exemplary embodiments include from about 1 mg to about 500 mg of the approved agent, e.g, from about 1 mg to about 200 mg, e.g., from about 5 mg to about 100 mg, e.g., from about 10 mg to about 60 mg.

In an exemplary embodiment, the unit dosage includes the approved agent carfilzomib and it is present in the liposome in an amount of from about 40 mg to about 80 mg, e.g., from about 50 mg to about 70 mg. In an exemplary embodiment, the carfilzomib is present in about 60 mg.

Active Loading

The process of active loading, involves the use of transmembrane potentials. The principle of active loading, in general, has been described extensively in the art. The terms active-loading and remote-loading are synonymous and will be used interchangeably.

During active loading, the precipitate of the sparingly water-soluble agent is transferred from the external aqueous medium across the liposomal membrane to the internal aqueous medium by a transmembrane proton- or ion-gradient. The term gradient of a particular compound as used herein refers to a discontinuous increase of the concentration of said compound across the liposomal membrane from outside (external aqueous medium) to inside the liposome (internal aqueous medium).

To create the concentration gradient, the liposomes are typically formed in a first liquid, typically aqueous, phase, followed by replacing or diluting said first liquid phase. The diluted or new external medium has a different concentration of the charged species or a totally different charged species, thereby establishing the ion- or proton-gradient.

The replacement of the external medium can be accomplished by various techniques, such as, by passing the lipid vesicle preparation through a gel filtration column, e.g., a Sephadex or Sepharose column, which has been equilibrated with the new medium, or by centrifugation, dialysis, or related techniques.

The efficiency of active-loading into liposomes depends, among other aspects, on the chemical properties of the complex to be loaded and the type and magnitude of the gradient applied. In an embodiment of the invention, a method as defined in any of the foregoing is provided employing a gradient across the liposomal membrane, in which the gradient is chosen from a pH-gradient, a sulfate-, phosphate-, phosphonate-, citrate-, or acetate-salt gradient, an EDTA-ion gradient, an ammonium-salt gradient, an alkylated, e.g methyl-, ethyl-, propyl- and amyl, ammonium-salt gradient, a $Mn^{2+}$-, $Cu^{2+}$-, $Na^+$-, $K^+$-gradient, with or without using ionophores, or a combination thereof. These loading techniques have been extensively described in the art.

Preferably, the internal aqueous medium of pre-formed, i.e., unloaded, liposomes comprises a so-called active-loading buffer which contains water and, dependent on the type of gradient employed during active loading, may further comprise a sulfate-, phosphate-, phosphonate-, citrate-, or acetate-salt, an ammonium-salt, an alkylated, e.g., methyl-, ethyl-, propyl- and amyl, ammonium-salt, an $Fe^{+2}$-, $Mn^{2+}$-, $Cu^{2+}$-$Na^+$ and/or $K^+$-salt, an EDTA-ion salt, and optionally a pH-buffer to maintain a pH-gradient. The salts may be polymeric such as dextran sulfate, polyethyleneimine, polyamidoamine dendrimers, the 1.5 carboxylate terminal version of polyamidoamines, polyphosphates, low molecular weight heparin, or hyaluronic acid. In an exemplary embodiment, the concentration of salts in the internal aqueous medium of unloaded liposomes is between 1 and 1000 mM.

The external aqueous medium, used to establish the transmembrane gradient for active loading, comprises water, the precipitate of the sparingly water-soluble agent(s) to be loaded, and optionally sucrose, saline or some other agent to adjust the osmolarity and/or a chelator like EDTA to aid ionophore activity, more preferably sucrose and/or EDTA.

In an exemplary embodiment the gradient is chosen from an amine or a metal salt of a member selected from a carboxylate, sulfate, phosphonate, phosphate or an acetate. As is generally known by those skilled in the art, transmembrane pH- (lower inside, higher outside pH) or cation acetate-gradients can be used to actively load amphiphilic weak acids. Amphipathic weak bases can also be actively loaded into liposomes using an ammonium sulfate- or triethylamine sulfate or ammonium chloride-gradient.

Carboxylates of use in the invention include, without limitation, carboxylate, citrate, diethylenetriaminepentaaceetate, melletic acetate, 1,2,3,4-butanetetracarboxylate, benzoate, isophalate, phthalate, 3,4-bis(carboxymethyl)cyclopentanecarboxylate, the carboxylate generation of polyamidoamine dendrimers, benzenetricarboxylates, benzenetetracarboxylates, ascorbate, glucuronate, and ulosonate.

Sulfates of use in the invention include, but are not limited to, sulfate, 1,5-naphthalenedisulfonate, dextran sulfate, sulfobutlyether beta cyclodextrin, sucrose octasulfate benzene sulfonate, poly(4-styrenesulfonate) trans resveratrol-trisulfate.

Phosphates and phosphonates of use in the invention include, but are not limited to, phosphate, hexametaphosphate, phosphate glasses, polyphosphates, triphosphate, trimetaphosphate, bisphosphonates, ethanehydroxy bisphosphonate, inositol hexaphosphate Exemplary salts of use in the invention include a mixture of carboxylate, sulfate or phosphate including but not limited to: 2-carboxybenensulfonate, creatine phosphate, phosphocholine, carnitine phosphate, the carboxyl generation of polyamidoamines.

Amines of use in the invention include, but are not limited to, monoamines, polyamines, trimethylammonium, triethylammonium, tributyl ammonium, diethylmethylammonium, diisopropylethyl ammonium, triisopropylammonium, N-methylmorpholinium, N-ethylmorpholinium, N-hydroxyethylpiperidinium, N-methylpyrrolidinium, N,N-dimethylpiperazinium, isopropylethylammonium, isopropylmethylammonium, diisopropylammonium, tert-butylethylammonium, dicychohexylammonium, protonized forms of morpholine, pyridine, piperidine, pyrrolidine, piperazine, imidazole, tert-butylamine, 2-amino-2-methylpropanol, 2-amino-2-methyl-propandiol, tris-(hydroxyethyl)-aminomethane, diethyl-(2-hydroxyethyl)amine, tris-(hydroxymethyl)-aminomethane tetramethylammonium, tetraethylammonium, N-methylglucamine and tetrabutylammonium, polyethyleneimine, and polyamidoamine dendrimers.

Depending upon the permeability of the lipid vesicle membranes, the full transmembrane potential corresponding to the concentration gradient will either form spontaneously or a permeability enhancing agent, e.g., a proton ionophore can be added to the medium. If desired, the permeability enhancing agent can be removed from the liposome preparation after loading with the complex is complete using chromatography or other techniques.

Typically the temperature of the medium during active loading is between about −25° C. and about 100° C., e.g., between about 0° C. and about 70° C., e.g., between about 4° C. and 65° C.

The encapsulation or loading efficiency, defined as encapsulated amount (e.g., as measured in grams of agent/moles of phospholipid or g of drug/g total lipid) of the sparingly water-soluble agent in the internal aqueous phase divided by the initial amount in the external aqueous phase multiplied by 100%, is at least 10%, preferably at least 50%, at least 90%.

In an exemplary embodiment, the invention provides a method of loading a sparingly water-soluble agent into a liposome. An exemplary method comprises, contacting an aqueous suspension of said liposome with an aqueous suspension of the agent under conditions appropriate to encapsulate the sparingly water-soluble agent in said liposome. The liposome has an internal aqueous environment encapsulated by a lipid membrane. The aqueous suspension of the liposome comprises a gradient selected from a proton gradient, an ion gradient and a combination thereof across the membrane. The sparingly water-soluble agent and the liposome suspension are incubated under conditions and for a selected time period appropriate for the sparingly water-soluble agent to traverse the membrane and concentrate in the internal aqueous environment, thereby forming said pharmaceutical formulation.

In various embodiments, the reaction mixture above is incubated for a selected period of time and the pH gradient, sulfate gradient, phosphate gradient, phosphonate gradient, carboxylate gradient (citrate gradient, acetate gradient, etc.), EDTA ion gradient, ammonium salt gradient, alkylated ammonium salt gradient, $Mg^{+2}$, $Mn^{+2}$, $Cu^{+2}$, $Na^+$, $K^+$ gradient or a combination thereof, exists across the liposomal membrane during the incubating.

In exemplary embodiments of the invention, the sparingly water-soluble therapeutic agent is not covalently attached to a component of the liposome, nor is it covalently attached to any component of the pH or salt gradient used to form the liposomal agent preparation of the invention.

Aprotic Solvent

In an exemplary embodiment, the sparingly water-soluble agent is completely dissolved in an aprotic solvent that is miscible with water. The agent solution is added to the aqueous liposome suspension at a concentration that is greater than the solubility of the drug agent in either the liposome suspension or the liposome suspension/aprotic solvent mixture, thus a precipitate is formed. Exemplary aprotic solvents include dimethylsulfoxide, dioxane, tetrahydrofuran, dimethylformamide, acetonitrile, dimethylacetamide, sulfolane, gamma butyrolactone, pyrrolidones, 1-methyl-2-pyrrolidinone, methylpyrroline, ethylene glycol monomethyl ether, diethylene glycol monomethyl ether, PEG400 and polyethylene glycols.

Sparingly Water-Soluble Agent Precipitate

The invention provides methods for loading of an insoluble precipitate inside the aqueous internal compartment of the lipid membrane of a liposome. An exemplary precipitate is conceptualized as some insoluble portion of the agent in suspension. The insoluble portion is defined as a portion of the agent that is not solvated as indicated by any of the following: any appearance of cloudiness greater than that of the liposome suspension in the absence of the agent, any degree of increased light scattering at a wavelength where the contents do not absorb light, such at 600 nm greater than the liposome suspension alone, any portion of the drug than can be isolated (pelleted) through centrifugation at a rate below 12,000 RPM for 15 min, any portion of the drug agent than can be isolated by filtration through 0.2 um filter.

Exemplary Formulation

In an exemplary embodiment, the invention provides a formulation of a sparingly water-soluble agent encapsulated within the aqueous core of a liposome comprising cholesterol, PEG-DSPE and a lipid component with a phopshocholine headgroup and one or two fatty acid residues. In various embodiments, the liposome comprises a combination of HSPC, cholesterol, and PEG-DSPE. In an exemplary embodiment, the liposome includes a molar ratio of components of from about 50 mole percent to about 70 mole percent HSPC, from about 25 mole percent to about 50 mole percent cholesterol and from about 0 mole percent to about 10 mole percent PEG-DSPE. In one embodiment, the liposome includes a molar ratio of components about 60 mole percent HSPC, about 40 mole percent cholesterol and about 2.8 mole percent PEG-DSPE. In an exemplary embodiment, the agent is encapsulated in the liposome by active loading.

In a further exemplary embodiment, the invention provides a formulation of a sparingly water-soluble agent encapsulated within the aqueous core of a liposome comprising a combination of sphingomyelin (SM), cholesterol, and PEG-DSPE. In an exemplary embodiment, the liposome includes a molar ratio of components from about 45 to about 75 SM, from about 25 mole percent to about 50 mole percent cholesterol and from about 0 mole percent to about 10 mole percent PEG-DSPE. In one embodiment, the liposome includes a molar ratio of components of about 55 mole percent SM, about 45 mole percent cholesterol and about 2.8 mole percent PEG-DSPE.

In an exemplary embodiment, the agent is carfilzomib or a salt, an analog or derivative thereof. In an exemplary embodiment, the carfilzomib:lipid ratio is from about 30 mg to about 90 mg of carfilzomib to from about 90 mg to about 250 mg of lipid. In an exemplary embodiment, the formulation the carfilzomid:lipid ratio is about 60 mg carfilzomib to about 170 mg lipid.

In various embodiments, the carfilzomib (µg): lipid (µmol) ratio is from about 250 to about 450. In an exemplary embodiment, this ratio is from about 300 to about 400.

In an exemplary embodiment, the remote loading agent is an ammonium salt of a carbohydrate sulfate. In various embodiments, the remote loading agent is triethylammonium dextran sulfate.

In an exemplary embodiment, the invention provides a pharmaceutical formulation comprising about 60 mg of carfilzomib encapsulated within a population of liposomes whose mass is from about 90 mg to about 200 mg. The liposomes comprise a lipid membrane defining an internal aqueous compartment. The carfilzomib is encapsulated within the aqueous compartment defined by the lipid membrane. The lipid membrane has a molar ratio of components: (a) of about 55 mole percent sphingomyelin (SM); (b) about 45 mole percent cholesterol; and (c) about 2.8 mole percent PEG-(1,2-distearoyl-sn-glycero-3-phosphoethanolamine) (PEG-DSPE). The formulation is selected from a lyophilized formulation and a formulation in which said liposomes are suspended in a pharmaceutically acceptable diluent.

In an exemplary embodiment, the invention provides a liposome formulation of carfilzomib in which the carfilzomib has an in vivo $T_{1/2}$ of from about 2 hours to about 12 hours, e.g., from about 3 hours to about 6 hours, in a subject to whom it is administered. In an exemplary formulation, the carfilzomib is in either free or encapsulated form.

An exemplary pharmaceutical formulation of the invention includes a liposome further encapsulating the carbohydrate sulfate. In an exemplary embodiment, the carbohydrate sulfate is dextran sulfate.

In an exemplary embodiment, the formulation of the invention is formed by a method comprising: (a) preparing a suspension of the liposome in an aqueous solution of an ammonium salt of a carbohydrate sulfate, forming a first population of said ammonium salt encapsulated within said liposome and a second population of said salt external to said liposome; (b) replacing the salt external to said liposome with an aqueous buffer, thereby forming a gradient of said carbohydrate sulfate across said lipid membrane; and (c) adding a solution of carfilzomib in an aprotic solvent to the suspension formed in (b), forming a carfilzomib precipitate capable of traversing said lipid membrane, concentrating in said internal aqueous compartment, thereby encapsulating said carfilzomib.

In an exemplary embodiment, the ammonium salt of the carbohydrate sulfate is triethylammonium dextran sulfate or ammonium dextran sulfate.

In an exemplary embodiment, the carfilzomib-loaded liposomes are from about 40 nm to about 150 nm in diameter.

In various embodiments, the encapsulated carfilzomib is solubilized in the internal aqueous compartment. In various embodiments, the carfilzomib is in the form of a suspension. In an exemplary embodiment, the carfilzomib fraction is partially solubilized and partially in the form of a suspension.

As will be appreciated by those of skill in the art, the individual parameters set forth above are freely combinable in any useful format.

Kits

In an exemplary embodiment, the invention provides a kit containing one or more components of the liposomes or formulations of the invention and instructions on how to combine and use the components and the formulation resulting from the combination. In various embodiments, the kit includes a sparingly water-soluble agent in one vessel and a liposome preparation in another vessel. An exemplary liposome preparation includes a distribution of salt on the outside and inside of the lipid membrane to establish and/or maintain an ion gradient, such as that described herein. Also included are instructions for combining the contents of the vessels to produce a liposome or a formulation thereof of the invention. In various embodiments, the amount of complex and liposome are sufficient to formulate a unit dosage formulation of the agent.

In an exemplary embodiment, one vessel includes a liposome or liposome solution, which is used to convert at least part of the contents of a vessel of a sparingly water-soluble therapeutic agent formulation (e.g., of an approved therapeutic agent) into a liquid formulation of the liposome encapsulated therapeutic agent at the point of care for administration to a subject. In an exemplary embodiment, the contents of the vessels are sufficient to formulate a unit dosage formulation of the therapeutic agent.

In the embodiment in which a unit dosage format is formed, the vessel includes from about 1 mg to about 500 mg of the therapeutic agent, e.g, from about 1 mg to about 200 mg, e.g., from about 5 mg to about 100 mg, e.g., from about 10 mg to about 60 mg.

In an exemplary embodiment, the approved therapeutic agent is carfilzomib and it is present in the vessel in an amount of from about 40 mg to about 80 mg, e.g., from about 50 mg to about 70 mg. In an exemplary embodiment, the carfilzomib is present in about 60 mg.

Methods of Treatment

In one aspect, the invention provides a method of treating a proliferative disorder, e.g., a cancer, in a subject, e.g., a human, the method comprising administering a composition that comprises a pharmaceutical formulation of the invention to a subject in an amount effective to treat the disorder, thereby treating the proliferative disorder.

In one embodiment, the pharmaceutical formulation is administered in combination with one or more additional anticancer agent, e.g., chemotherapeutic agent, e.g., a chemotherapeutic agent or combination of chemotherapeutic agents described herein, and radiation.

In one embodiment, the cancer is a cancer described herein. For example, the cancer can be a cancer of the bladder (including accelerated and metastatic bladder cancer), breast (e.g., estrogen receptor positive breast cancer; estrogen receptor negative breast cancer; HER-2 positive breast cancer; HER-2 negative breast cancer; progesterone receptor positive breast cancer; progesterone receptor negative breast cancer; estrogen receptor negative, HER-2 negative and progesterone receptor negative breast cancer (i.e., triple negative breast cancer); inflammatory breast cancer), colon (including colorectal cancer), kidney (e.g., transitional cell carcinoma), liver, lung (including small and non-small cell lung cancer, lung adenocarcinoma and squamous cell cancer), genitourinary tract, e.g., ovary (including fallopian tube and peritoneal cancers), cervix, prostate, testes, kidney, and ureter, lymphatic system, rectum, larynx, pancreas (including exocrine pancreatic carcinoma), esophagus, stomach, gall bladder, thyroid, skin (including squamous cell carcinoma), brain (including glioblastoma multiforme), head and neck (e.g., occult primary), and soft tissue (e.g., Kaposi's sarcoma (e.g., AIDS related Kaposi's sarcoma), leiomyosarcoma, angiosarcoma, and histiocytoma).

In an exemplary embodiment, the cancer is multiple myeloma or a solid tumor. In one embodiment, the pharmaceutical formulation of the invention includes carfilzomib as the sparingly water-soluble therapeutic agent.

In one aspect, the disclosure features a method of treating a disease or disorder associated with inflammation, e.g., an allergic reaction or an autoimmune disease, in a subject, e.g., a human, the method comprises: administering a composition that comprises a pharmaceutical formulation of the invention to a subject in an amount effective to treat the disorder, to thereby treat the disease or disorder associated with inflammation.

In one embodiment, the disease or disorder associated with inflammation is a disease or disorder described herein. For example, the disease or disorder associated with inflammation can be for example, multiple sclerosis, rheumatoid arthritis, psoriatic arthritis, degenerative joint disease, spondouloarthropathies, gouty arthritis, systemic lupus erythematosus, juvenile arthritis, rheumatoid arthritis, osteoarthritis, osteoporosis, diabetes (e.g., insulin dependent diabetes mellitus or juvenile onset diabetes), menstrual cramps, cystic fibrosis, inflammatory bowel disease, irritable bowel syndrome, Crohn's disease, mucous colitis, ulcerative colitis, gastritis, esophagitis, pancreatitis, peritonitis, Alzheimer's disease, shock, ankylosing spondylitis, gastritis, conjunctivitis, pancreatitis (acute or chronic), multiple organ injury syndrome (e.g., secondary to septicemia or trauma), myocardial infarction, atherosclerosis, stroke, reperfusion injury (e.g., due to cardiopulmonary bypass or kidney dialysis), acute glomerulonephritis, vasculitis, thermal injury (i.e., sunburn), necrotizing enterocolitis, granulocyte transfusion associated syndrome, and/or Sjogren's syndrome. Exemplary inflammatory conditions of the skin include, for example, eczema, atopic dermatitis, contact dermatitis, urticaria, scleroderma, psoriasis, and dermatosis with acute inflammatory components. In some embodiments, the autoimmune disease is an organ-tissue autoimmune diseases (e.g., Raynaud's syndrome), scleroderma, myasthenia gravis, transplant rejection, endotoxin shock, sepsis, psoriasis, eczema, dermatitis, multiple sclerosis, autoimmune thyroiditis, uveitis, systemic lupus erythematosis, Addison's disease, autoimmune polyglandular disease (also known as autoimmune polyglandular syndrome), or Grave's disease.

In another embodiment, a pharmaceutical formulation of the invention or method described herein may be used to treat or prevent allergies and respiratory conditions, including asthma, bronchitis, pulmonary fibrosis, allergic rhinitis, oxygen toxicity, emphysema, chronic bronchitis, acute respiratory distress syndrome, and any chronic obstructive pulmonary disease (COPD). The pharmaceutical formulation of the invention, particle or composition may be used to treat chronic hepatitis infection, including hepatitis B and hepatitis C.

In one aspect, the disclosure features a method of treating cardiovascular disease, e.g., heart disease, in a subject, e.g., a human, the method comprising administering a pharmaceutical formulation of the invention to a subject in an amount effective to treat the disorder, thereby treating the cardiovascular disease.

In one embodiment, cardiovascular disease is a disease or disorder described herein. For example, the cardiovascular disease may be cardiomyopathy or myocarditis; such as idiopathic cardiomyopathy, metabolic cardiomyopathy, alcoholic cardiomyopathy, drug-induced cardiomyopathy, ischemic cardiomyopathy, and hypertensive cardiomyopathy. Also treatable or preventable using a pharmaceutical formulation of the inventions, particles, compositions and methods described herein are atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries. Other vascular diseases that can be treated or prevented include those related to platelet aggregation, the retinal arterioles, the glomerular arterioles, the vasa nervorum, cardiac arterioles, and associated capillary beds of the eye, the kidney, the heart, and the central and peripheral nervous systems. Yet other disorders that may be treated with pharmaceutical formulation of the invention, include restenosis, e.g., following coronary intervention, and disorders relating to an abnormal level of high density and low density cholesterol.

In one embodiment, the pharmaceutical formulation of the invention can be administered to a subject undergoing or who has undergone angioplasty. In one embodiment, the Pharmaceutical formulation of the invention, particle or composition is administered to a subject undergoing or who has undergone angioplasty with a stent placement. In some embodiments, the pharmaceutical formulation of the invention, particle or composition can be used as a strut of a stent or a coating for a stent.

In one aspect, the invention provides a method of treating a disease or disorder associated with the kidney, e.g., renal disorders, in a subject, e.g., a human, the method comprises: administering a pharmaceutical formulation of the invention to a subject in an amount effective to treat the disorder, thereby treating the disease or disorder associated with kidney disease.

In one embodiment, the disease or disorder associated with the kidney is a disease or disorder described herein. For example, the disease or disorder associated with the kidney can be for example, acute kidney failure, acute nephritic syndrome, analgesic nephropathy, atheroembolic renal disease, chronic kidney failure, chronic nephritis, congenital nephrotic syndrome, end-stage renal disease, good pasture syndrome, interstitial nephritis, kidney damage, kidney infection, kidney injury, kidney stones, lupus nephritis, membranoproliferative GN I, membranoproliferative GN II, membranous nephropathy, minimal change disease, necrotizing glomerulonephritis, nephroblastoma, nephrocalcinosis, nephrogenic diabetes insipidus, nephrosis (nephrotic syndrome), polycystic kidney disease, post-streptococcal GN, reflux nephropathy, renal artery embolism, renal artery stenosis, renal papillary necrosis, renal tubular acidosis type I, renal tubular acidosis type II, renal underperfusion, renal vein thrombosis.

In an exemplary embodiment, the invention provides a method of treating metal toxicity or metal overload. Examples of diseases or disorders associated with metal include iron overload disorders (e.g., thalassemia or sickle cell anemia), copper over load disorders (e.g., Wilson's disease), and radioisotope contamination (e.g., occurring subsequent to contamination with plutonium, uranium and other radioistopes).

An "effective amount" or "an amount effective" refers to an amount of the pharmaceutical formulation of the invention which is effective, upon single or multiple dose administrations to a subject, in treating a cell, or curing, alleviating, relieving or improving a symptom of a disorder. An effective amount of the composition may vary according to factors such as the disease state, age, sex, and weight of the individual, and the ability of the compound to elicit a desired response in the individual. An effective amount is also one in which any toxic or detrimental effects of the composition are outweighed by the therapeutically beneficial effects.

As used herein, the term "prevent" or "preventing" as used in the context of the administration of an agent to a subject, refers to subjecting the subject to a regimen, e.g., the administration of a pharmaceutical formulation of the invention such that the onset of at least one symptom of the disorder is delayed as compared to what would be seen in the absence of the regimen.

As used herein, the term "subject" is intended to include human and non-human animals. Exemplary human subjects include a human patient having a disorder, e.g., a disorder described herein, or a normal subject. The term "non-human animals" includes all vertebrates, e.g., non-mammals (such as chickens, amphibians, reptiles) and mammals, such as non-human primates, domesticated and/or agriculturally useful animals, e.g., sheep, dog, cat, cow, pig, etc.

As used herein, the term "treat" or "treating" a subject having a disorder refers to subjecting the subject to a regimen, e.g., the administration of a pharmaceutical formulation of the invention such that at least one symptom of the disorder is cured, healed, alleviated, relieved, altered, remedied, ameliorated, or improved. Treating includes administering an amount effective to alleviate, relieve, alter, remedy, ameliorate, improve or affect the disorder or the symptoms of the disorder. The treatment may inhibit deterioration or worsening of a symptom of a disorder.

The following examples are provided to illustrate exemplary embodiments of the invention and are not to be construed as limiting the scope of the invention.

EXAMPLES

Example 1

Carfilzomib Liposome Entrapment by Remote Loading
Materials and Method

Ammonium sulfate solution was prepared by dissolving ammonium sulfate solid to a final concentration of 250 mM (500 mequivilents of anion/L) no pH adjustment was made to yield a final pH of 5.6. Sodium sulfate solution (250 mM) was prepared by adding 0.35 g sodium sulfate to 10 mL deionized water.

The liposomes were formed by extrusion. Lipids were dissolved in ethanol at a concentration of 500 mM HSPC (591 mg/mL total lipid) at 65° C. and the 9 volumes of the trapping agent solution heated to 65° C. was added to the ethanol/lipid solution also at 65° C. The mixture was vortexed and transferred to a 10 mL thermostatically controlled (65° C.) Lipex Extruder. The liposomes were formed by extruding 10 times through polycarbonate membranes having 0.1 um pores. After extrusion the liposomes were cooled on ice. The transmembrane electrochemical gradient was formed by purification of the liposomes by dialysis in dialysis tubing having a molecular weight cut off of 12,000-14,000. The samples are dialyzed against 5 mM HEPES, 10% sucrose pH 6.5 (stirring at 4° C.) at volume that is 100 fold greater than the sample volume. The dialysate was changed after 2 h then 4 more times after 12 h each. The conductivity of the liposome solution was measured and was indistinguishable from the dialysis medium ~40 μS/cm.

The lipid concentration is determined by measuring the cholesterol by HPLC using an Agilent 1100 HPLC with and Agilent Zorbax 5 um, 4.6×150 mM, Eclipse XDB-C8 column and a mobile phase of A=0.1% TFA, B=0.1% TFA/MeOH with an isocratic elution of 99% B. The flow rate is 1.0 mL/min, column temperature is 50° C., 10 μL injection and detection by absorbance at 205 nm. The retention time of cholesterol is 4.5 min. The liposome size is measured by dynamic light scattering.

Carfilzomib (Selleck Chemicals) was dissolved in DMSO at a concentration of 10 mg/mL. The carfilzomib was introduced to the liposomes at a carfilzomib to HSPC ratio of 100 g drug/mol HSPC (drug to total lipid ratio (wt/wt) of 0.12). The liposomes were diluted with 50 mM citrate, 10% sucrose pH 4.0 to increase the volume to a point where after addition of the drug the final DMSO concentration is 2%. The carfilzomib/DMSO was added to the diluted liposomes, which were mixed at room temperature then transferred to a 65° C. bath and swirled every 30 s for the first 3 min and then swirled every 5 min over a total heating time of 30 min. All samples were very cloudy when the drug was added and all became clear (same as liposomes with no drug added) after 15 min. After heating for 30 min all samples were placed on ice for 15 min. The loaded liposomes were vortexed and 100 μL of sample was kept as the "before column" and the rest transferred to microcentrifuge tubes and spun at 10,000 RPM for 5 min. The supernatants were purified on a Sephadex G25 column collected and analyzed by HPLC. The HPLC analysis of carfilzomib was performed on the same system as described for analysis of cholesterol. The mobile phase consists of A=0.1% TFA, B=0.1% TFA/MeOH with a gradient elution starting at 50% B and increasing to 83% B in 13 min with 7 min equilibration back to 50% B. The flow rate is 1.0 mL/min, column temperature is 30 C, 10 μl injection and detection by absorbance at 205 nm. The retention time of carfilzomib is 12.2 min. The lipid concentration is determined by analysis of the cholesterol by HPLC.

Results

Figure 2:
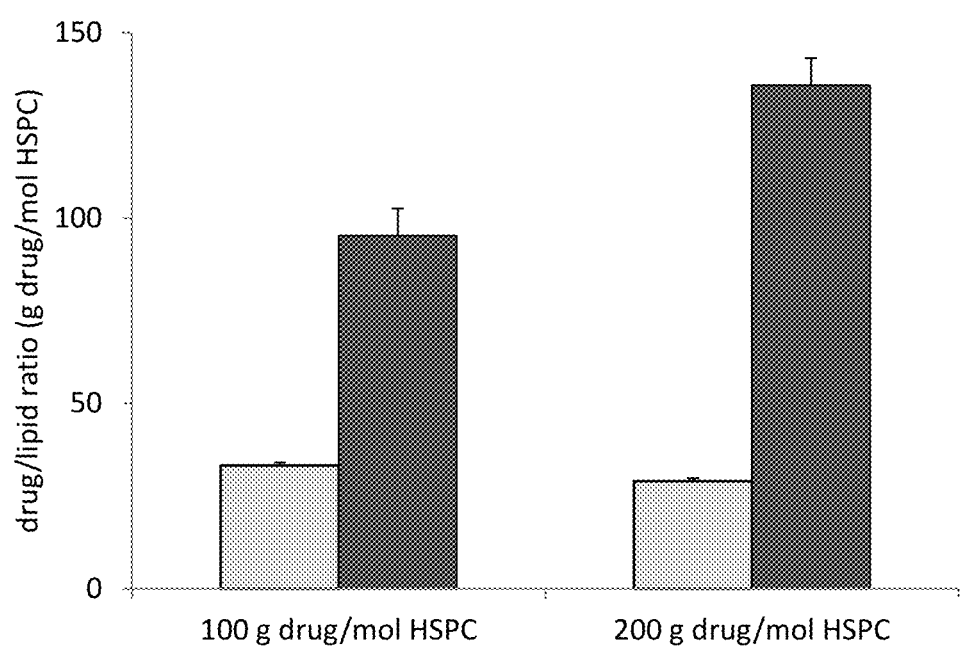
FIG. 2. Liposome formulations composed of HSPC/Chol/Peg-DSPE containing either sodium sulfate (light shade) or ammonium sulfate (dark shade) were incubated with carfilzomib at two input drug-to-lipid ratios using conditions described below. The liposomes were purified from unencapsulated drug and the amount of encapsulated carfilzomib within the liposomes is shown, expressed as µg of carfilzomib per µmol lipid.
Figure 5:
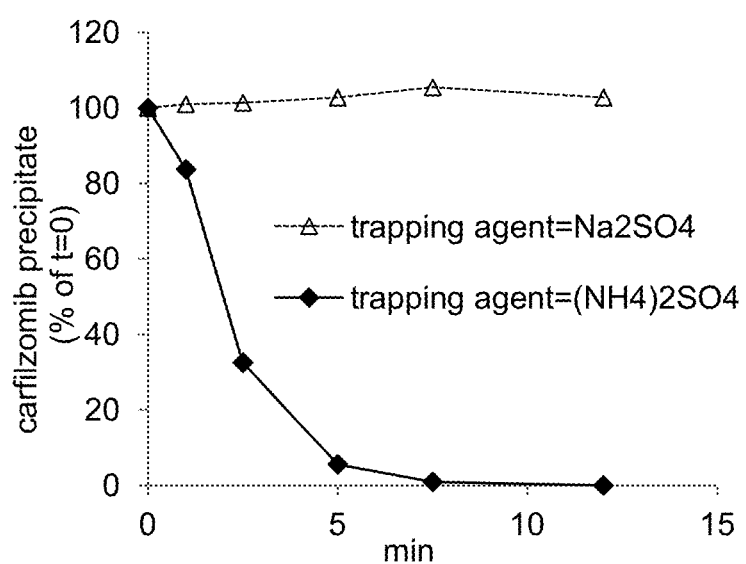
FIG. 5 is a line graph showing carfilzomib loading from precipitate demonstrated by reduction of light scattering at 600 nm.

The loading of liposomes containing 250 mM ammonium sulfate resulted in a final drug to lipid ratio of 95.26±3.47 g drug/mol of HSPC liposomes when the drug was added at 100 g drug/mol of HSPC lipid (95.26±3.47% efficient) and a final drug to lipid ratio of 136.9±7.35 g drug/mol of HSPC liposomes when the drug was added at 200 g drug/mol of HSPC lipid (67.94±3.67% efficient) (FIG. 2). This demonstrates that the loading capacity of these particular liposomes is between 100 and 200 g drug/mol phospholipid. The control liposomes containing 250 mM sodium sulfate which have no electrochemical gradient for remote loading resulted in a final drug load of 33.28±0.79 and 29.01±0.79 g drug/mol of HSPC when the drug was added at a ratio of 100 and 200 g drug/mol of HSPC respectively. This demonstrates that the capacity for loading these liposomes was saturated below 100 g drug/mol of HSPC and at this drug input ratio the remote loaded liposomes exhibit >3 fold higher loading capacity. Saturation of the drug loading capacity for sodium sulfate liposomes at a ratio at least 3 fold lower than the ammonium sulfate liposomes indicates that when no electrochemical gradient is present for remote loading the drug partitions into the lipid bilayer but does not form a salt with the interior trapping agent. FIG. 5 illustrates the precipitate is still present after the loading process with sodium sulfate liposomes but not with ammonium sulfate liposomes.

Conclusion

Liposomes of identical lipid matrix composition and size but varying in the composition of the sulfate salt internally trapped had very different capabilities to load carfilzomib. The liposome capable of generating an electrochemical gradient (ammonium sulfate) was able to load close to 100% of the drug at optimal conditions and the one incapable of creating a gradient had poor loading efficiency suggesting that remote or active loading was the primary mechanism for carfilzomib incorporation into the liposome.

Example 2

Comparison of Liposome Trapping Agents

Introduction

Liposomes to be used for remote loading are formed in an ionic solution that is intended to complex the loaded drug as a salt. Trapping agents can form complexes with loaded drugs and the stability of this complex is one factor that dictates liposome drug loading ability, stability and drug release rates. Comparison of different liposome trapping agents was made by evaluating the efficiency of carfilzomib loading.

Methods

Three liposome formulations were used, all at a molar ratio 3 HSPC/2 Chol/0.15 PEG-DSPE each with a different trapping agent: 1. mellitic acid; 2. ammonium sulfate; and 3. napthelene disulfononic acid.

Mellitic acid (MA) was dissolved in water and titrated with diethylamine to a final pH of 5.5 and concentration of 83 mM (500 mequivilents of anion/L). Ammonium sulfate was prepared by dissolving ammonium sulfate solid to a final concentration of 250 mM (500 mequivilents of anion/L) no pH adjustment was made to yield a final pH of 5.6.

Napthelenedisulfonic acid (NDS) was dissolved in water and titrated with diethylamine to a final pH of 8.0 and concentration of 250 mM (500 mequivilents of anion/L).

See Example 1, Carfilzomib liposome entrapment by remote loading for details on how the liposomes were made, purified and characterized.

TABLE 1

Sizes of Liposomes Loaded with Carfilzomib.

| Trapping agent | before lyophilizing | |
|---|---|---|
| | Z-ave (nm) | PDI |
| (NH4)$_2$SO$_4$ (Drug added quickly) | 108 | 0.062 |
| (NH4)$_2$SO$_4$ (Drug added slowly) | 109.2 | 0.035 |
| Napthelenedisulfonic acid | 111.9 | 0.039 |
| Mellitic Acid | 105.5 | 0.08 |

To ensure complete removal of the DMSO added with carfilzomib, the liposomal carfilzomib samples were dialyzed in dialysis tubing having a molecular weight cut off of 12,000-14,000. The samples are dialyzed against 5 mM HEPES, 10% sucrose pH 6.5 (stirring at 4° C.) at volume that is 100 fold greater than the sample volume. The dialysate was changed after 2 h then 2 more times after 12 h each. The carfilzomib liposomes were again analyzed for drug and lipid concentration as described above.

Results

Figure 3:
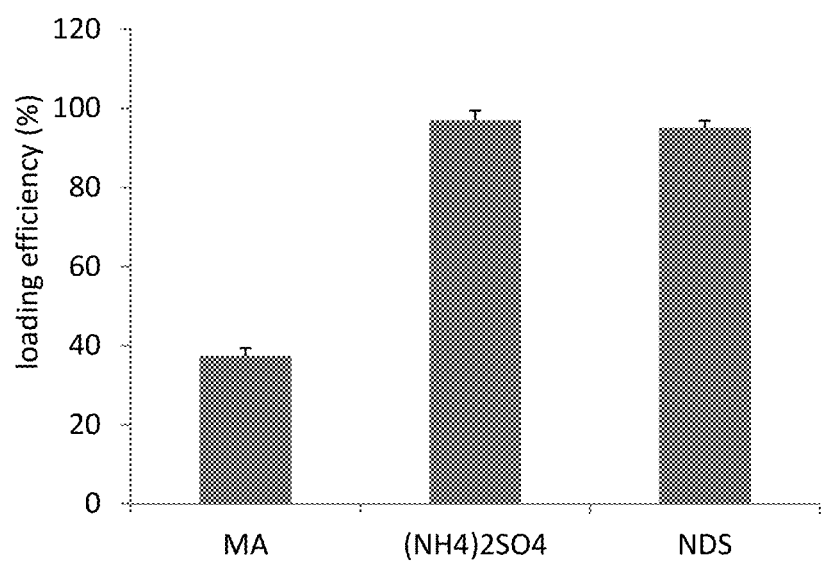
FIG. 3 is a bar graph showing a trapping agent effect on liposome loading of carfilzomib.

The efficiency of carfilzomib remote loading into liposomes at 100 g drug/mol of HSPC lipid for liposomes with the trapping agents mellitic acid, ammonium sulfate, and napthelenedisulfonic acid were 37.4%±2.01%, 97.0%±2.38%, and 95.1%±1.76% respectively (FIG. 3).

Conclusion

The invention described here enables remote loading of carfilzomib from an insoluble precipitate into liposomes can be accomplished with various using the electrochemical gradient generated by various trapping agents including mellitic acid, ammonium sulfate and napthelene disulfononic acid.

Example 3

Comparison of Method for Introducing Drug

Method

A comparison of the method used for addition of the drug to the liposomes during the loading procedure. The loading procedure was the same as described above in Example 1 with the exception of the drug being added to the liposome loading solution as a solid powder, followed by the addition of DMSO to a final concentration of 2% (vol/vol), as a 10 mg/mL DMSO solution quickly and as 10 mg/mL DMSO solution slowly (both at a final DMSO content of 2% (vol/vol).

Results

Figure 4:
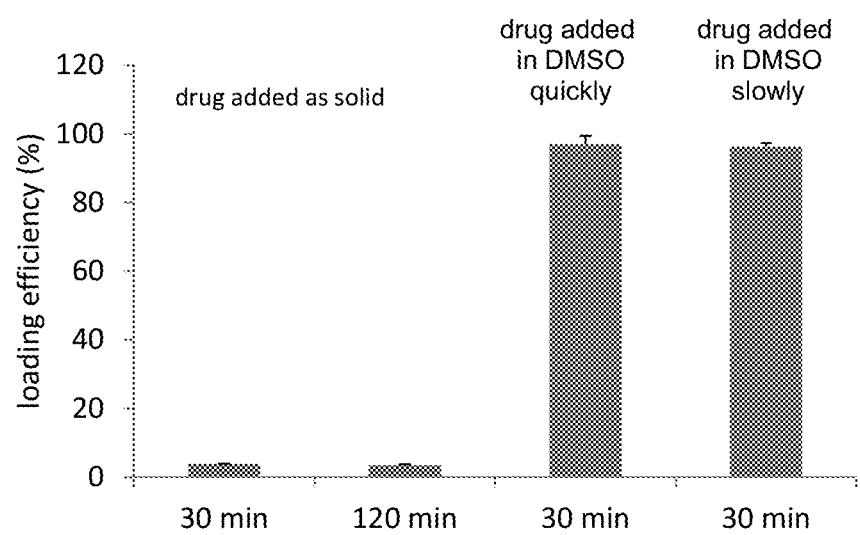
FIG. 4 is a bar graph showing a method of drug introduction effect on liposome loading of carfilzomib.

The efficiency of carfilzomib remote loading into liposomes at 100 g drug/mol of HSPC lipid for the drug which was first added as the solid powder was 3.88%±0.053% and 3.47%±0.030% when heated to 65° C. for 30 and 120 min respectively. The efficiency of loading the drug from initial stock solutions of 10 mg/mL DMSO solution was 97.0%±2.38% when the drug/DMSO was added quickly and 96.3%±1.09% when the drug/DMSO was added in 5 increments over 1 min to a liposome solution while vortexing. The drug/liposome mixture that results from the slow drug addition is clearer than the drug/liposome mixture that results from rapid addition of the drug. However, both solutions have no visible precipitate (or centrifugal precipitate at 10,000 rpm for 5 min) after heating to 65° C. for 30 min, which is a result of all of the drug being loaded into the liposomes regardless of the precipitate formed upon addition of the drug (FIG. 4). This shows that having the drug initially fully dissolved in the aprotic solvent prior to diluting beyond its solubility limit into an aqueous solution is useful for remote loading into liposomes containing a pH or ion gradient.

Example 4

Carfilzomib Loading into Liposomes at Room Temperature
Introduction

The ability to load a drug into liposomes at room temperature is beneficial to reduce heat-induced drug degradation, simplify manufacturing and allow for bedside liposome loading. Efficient transport across the liposome membrane requires the membrane to be in a fluid phase. This is accomplished with saturated phospholipids having a high phase transition temperature ($T_m$) such as HSPC ($T_m=55°$ C.) by heating the liposomes above the $T_m$ during the loading process. An alternative to heating is to use lipids that are fluid phase at room temperature. The disadvantage of these lipids is that they are unstable in circulation and result in rapid drug release. Sterol modified lipids incorporate a novel lipid construction where cholesterol (sterol) is covalently attached to the phosphate headgroup. Sterol modified lipids have proven to render the sterol non-exchangable from the lipid bilayer in circulation. Sterol modified lipids are also fluid phase at room temperature, making them ideal for room temperature loading of drugs into liposomes that are to be used for in vivo delivery of therapeutics.
Method The loading of carfilzomib into liposomes at room temperature was performed by using two liposome formulations composed of a molar ratio of 95 PChemsPC/5 PEG-DSPE and another with a molar ratio of 3 POPC/2 Chol/0.15 PEG-DSPE each containing 250 mM ammonium sulfate as the trapping agent. The liposomes were prepared using the procedure, drug/liposome ratio, buffers ad pH as described in Example 1. The liposomes were stirred at room temperature (20° C.) and the carfilzomib was added as a 10 mg/mL DMSO solution in 5 increments over 1 min to result in a cloudy solution. The liposome/drug mixture was stirred at room temperature for a total of 30 min to yield a clear solution with the same appearance as the liposome solution before the drug was added.
Results The efficiency of carfilzomib remote loading into liposomes at 100 g drug/mol of PChemsPC was 95.5%±1.23% The efficiency of carfilzomib remote loading into liposomes at 187 g drug/mol of 3 POPC/2 Chol/0.15 PEG-DSPE was 100.52%±1.01%
Conclusion The invention described here was not able to load carfilzomib into liposomes by adding the crystal form of the drug directly to the loading solution. The drug requires solubilization in some solvent prior to addition to the loading solution at a concentration above the solubility of the drug. Liposome loading efficiency of the precipitate that is formed upon addition of the drug to the loading solution is not dependent upon the rate of addition in this case using carfilzomib.

Example 5

Drug Precipitate Loading into Liposomes as Determined by Light Scattering at 600 nm.
Introduction Liposome loading of drug from a precipitate into liposomes is evidenced by the resulting drug to lipid ratio and clarifying of the solution as the drug precipitate transfers into the liposome. To get a quantitative measure liposome loading from a drug precipitate the light scattering was measured at 600 nm during the loading process.
Method Liposomes containing 250 mM ammonium sulfate as trapping agent and 250 mM sodium sulfate as control liposomes which would not remote load drug. The liposomes were prepared and loaded using the procedure described in Example 1 except a disposable polystyrene cuvette was used as the reaction vessel. The scattering of light at 600 nm was measured with a UV/vis spectrophotometer during the loading process.
Results/Conclusion The sodium sulfate liposomes do not show any clarification of the precipitate during the loading procedure indication that the drug is not remote loading into the liposomes. (see FIG. 5). The ammonium sulfate liposomes efficiently load the drug resulting in clarification of the solution within 15 min.

Example 6

Confirmation of Drug Release from Remote Loaded Liposomes
Introduction

A reverse gradient was used to attempt to release the active drug from within the liposome. The theory is that if a drug can be released from within a liposome with a reverse gradient there is a high probability the that drug release will occur in vivo.
Method Liposomes were loaded with carfilzomib as described in Example 1 and were purified into deionized water. The sample was divided into two aliquots. To the first aliquot, concentrated Hepes pH 7.4 and NaCl was added so that the final concentration was 5 mM Hepes, 145 mM NaCl (HBS). To the second aliquot, concentrated ammonium sulfate was added so that the final concentration was 250 mM. No obvious physical changes were initially observed. The samples were then heated at 65° C. for 30 min. The samples were transferred to clean eppendorf tubes and centrifuged for 10,000 rpm for 5 min after which the supernatants and precipitates were separated and tested for carfilzomib content by HPLC assay. Released drug precipitated, liposome encapsulated drug remained in the supernatant. The % carfilzomib released was calculated by $$\% \text{ Release} = \frac{amt. \text{ of drug in precipitate}}{amt. \text{ of total drug}}$$

Results

TABLE 2

The reverse gradient-directed drug release from liposomes

| Solution Composition | % Carfilzomib Released |
|---|---|
| Hepes buffered saline | 10.6 ± 0.28 |
| Ammonium sulfate | 68.5 ± 1.82 |

Figure 6:
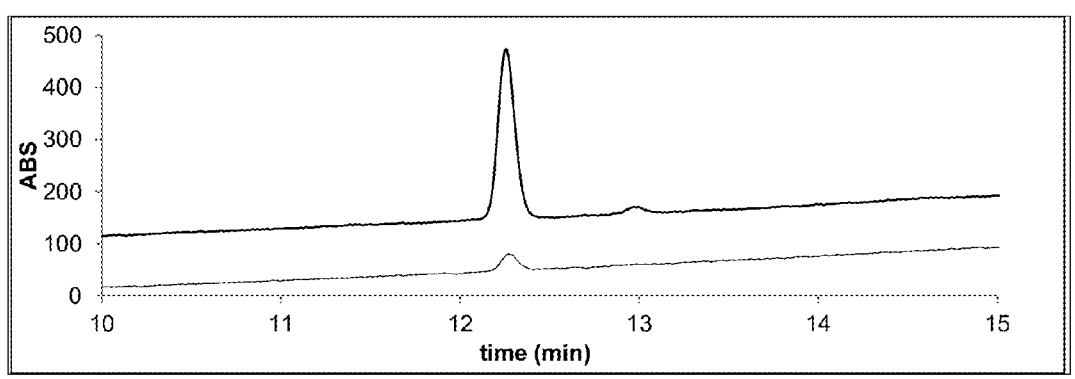
FIG. 6 is a HPLC Chromatogram of Carfilzomib before loading into liposomes (upper) and after loading into liposomes from a precipitate and then being released from liposomes using a reverse ammonium sulfate gradient where it is converted back to a precipitate in the extraliposomal solution (lower).
Figure 7:
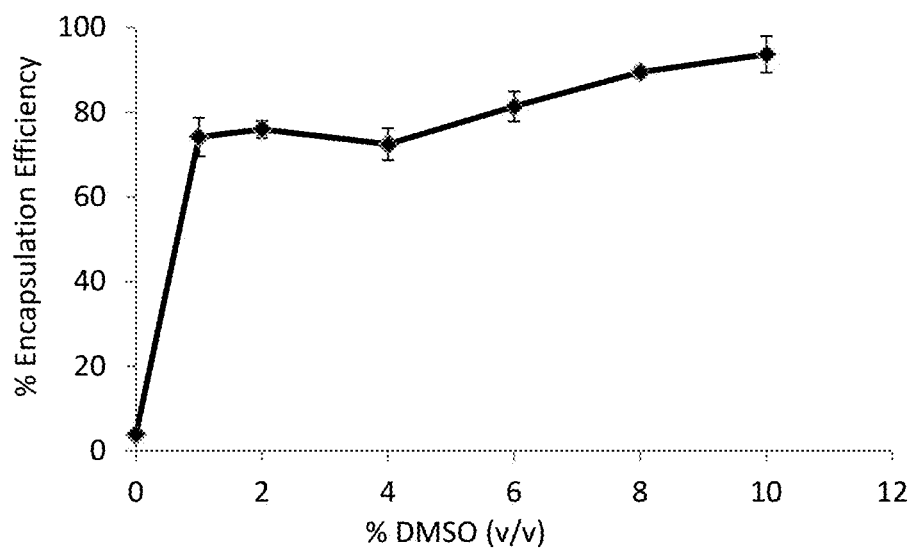
FIG. 7 is a line graph showing liposome encapsulation efficiency as a function of [DMSO]. The input drug-to-lipid ratio was 200 μg/μmol.

The drug released using the reverse gradient is 6.5-fold greater than the drug released from the control with no reverse gradient (Table 2). HPLC chromatogram of the released drug was identical to the starting material indicating that no degradation of carfilzomib had taken place (FIG. 7). HPLC retention time for the stock solution of carfilzomib was 12.2 min and the retention time for the carfilzomib that was released from the remote loaded liposome was 12.3 min, as shown in FIG. 6. These two separations times are within the variability of the HPLC system and are not statistically different from each other.

Conclusion

Carfilzomib was released from the liposome using a reverse gradient to yield the original molecule as indicated by HPLC analysis.

Example 7

Carfilzomib Loading as a Function of DMSO Content

Introduction

The physical form of the drug when added to liposomes is important for loading efficiency, i.e., when added as a dry powder almost no loading is observed but addition using a predissolved solution in an aprotic solvent can lead to high entrapment efficiency. This study looks at the effect of aprotic solvent concentration on drug loading efficiency of carfilzomib.

Method

Ammonium sulfate containing liposomes were diluted in 50 mM citric acid sucrose (10% wt/wt) buffer pH 4.0 to 1 mM phospholipid. Various amounts of DMSO were added so that when 200 μg drug was added from a 10 mg/mL carfilzomib solution in DMSO the final DMSO concentration ranged from 1-10% v/v.

Results

DMSO had a dramatic effect on the ability of carfilzomib to remote load into liposomes. When absent, there is practically no loading. At concentrations 1% and above the loading efficiency ranges from 74-94%, with higher efficiencies observed at higher DMSO concentrations (FIG. 7). It should be noted that drug precipitates were observed in all samples before loading commenced, suggesting that the concentrations of DMSO used here are below the minimum concentration required to effectively solubilize carfilzomib at the drug concentration used (0.2 mg/mL).

Conclusions

The introduction of pre-solubilized carfilzomib is necessary for efficient remote loading. However, above 1% DMSO there is a relatively small change in loading efficiency, up as far as 10%.

Example 8

Carfilzomib Solubility as a Function of DMSO Content

Introduction

Under the conditions described above, carfilzomib is solubilized in DMSO before diluting in liposome buffer solution prior to loading. It then immediately precipitates before remote loading. This study is designed to determine the DMSO concentration that is required to effectively solubilize carfilzomib at room temperature and at the temperature required for liposome loading into liposomes composed of high Tm lipids (65° C.).

Method

Figure 8:
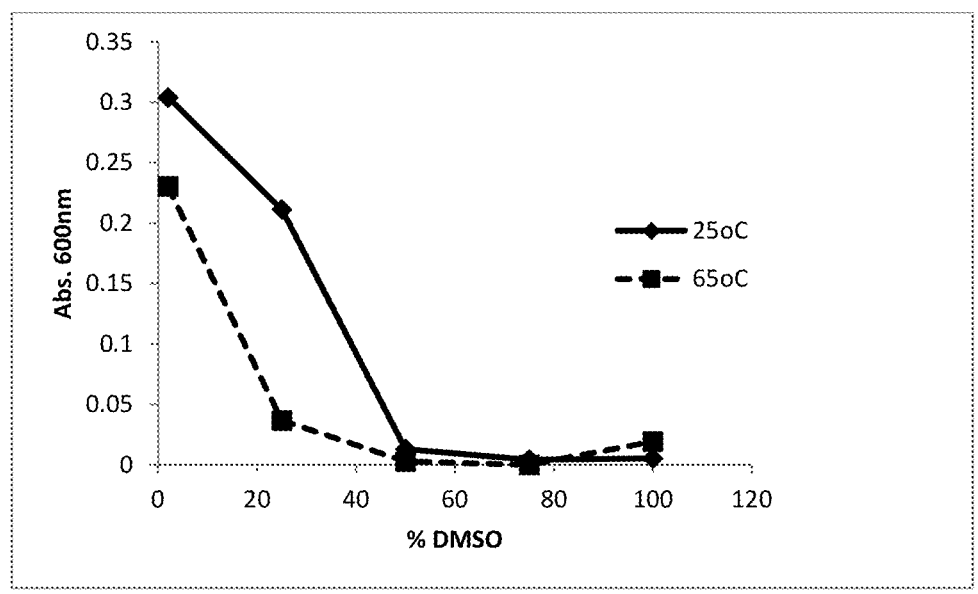
FIG. 8 is a line graph showing light scattering of carfilzomib solutions a function of DMSO concentration. The concentration of carfilzomib was 0.2 mg/mL.
Figure 9:
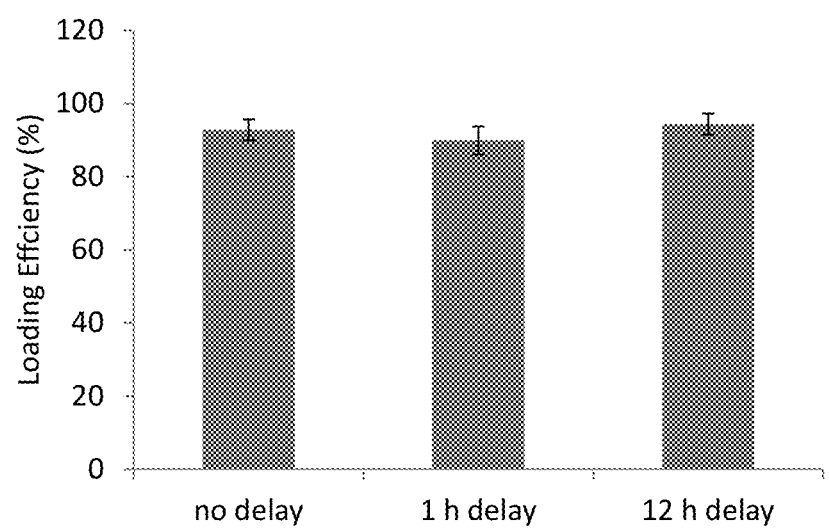
FIG. 9 is a bar graph showing the effect of delay time between the formation of drug precipitate and liposome loading of the precipitate.
Figure 10:
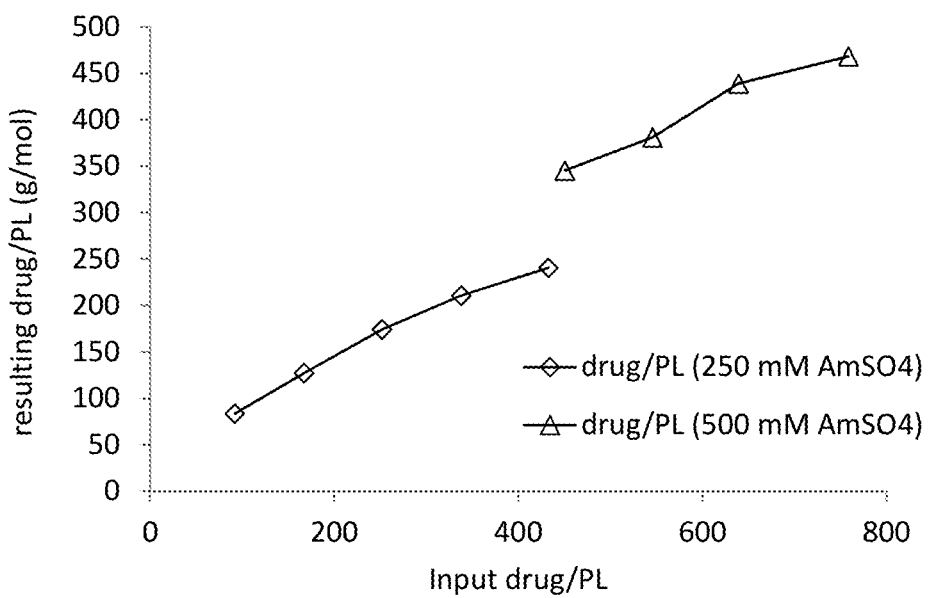
FIG. 10 is a line graph showing the effect of ammonium sulfate trapping agent concentration on liposome drug payload of carfilzomib loaded from a precipitate.
Figure 11:
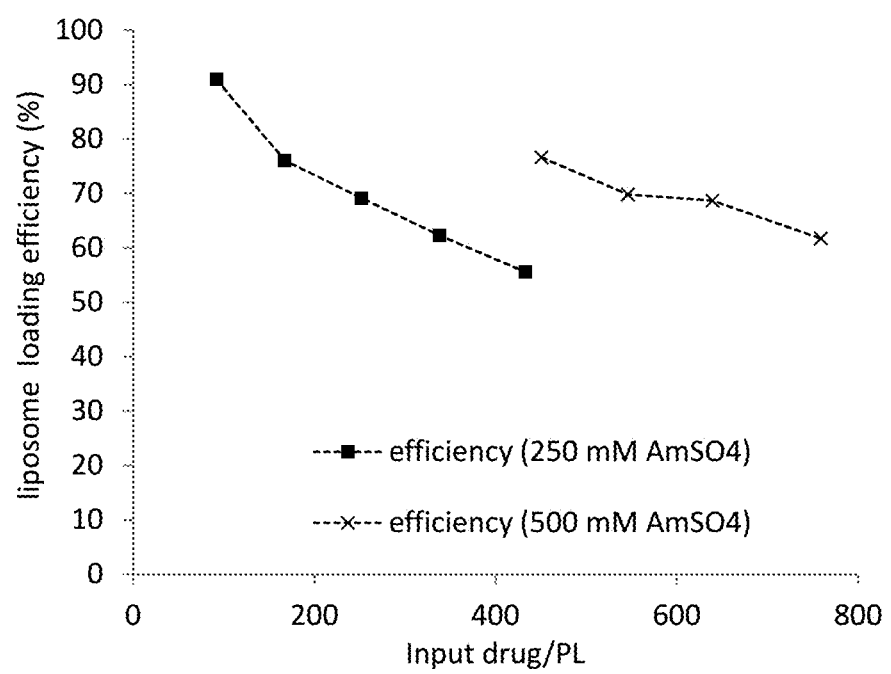
FIG. 11 is a line graph showing effect of ammonium sulfate trapping agent concentration on liposome loading efficiency of carfilzomib from precipitate.

Carfilzomib was added from a stock 10 mg/mL solution in DMSO to 1 mL of a citric acid/DMSO mixture so that the composition of DMSO was 2%, 25%, 50%, 75% and 100%. The final drug concentration was 0.2 mg/mL. The solutions were prepared and measured for optical density at 600 nm. The optical density at 600 nm is a good measure of how turbid or how much scattering material (such as drug precipitates) are in a solution, generally, the more precipitates the higher the absorbance. From FIG. 8 is apparent that at DMSO concentrations below 50% vol/vol (25° C.) and 25% vol/vol (65° C.) the drug remains in a precipitated form. Only when the concentration of DMSO is increased does it become effectively solubilized at this concentration of 0.2 mg/mL.

To test the integrity of the liposomes in 25% DMSO we attempted to remote load the water-soluble weak base drugs doxorubicin and 17-dimethylaminoethylamino-17-demethoxygeldanamycin (17-DMAG) and compared to the same loading without DMSO. We found that the loading efficiency was adversely affected (Table 3).

Results

At 0.2 mg/mL carfilzomib the drug precipitates and the aggregates are large enough to cause a light scattering signal at 600 nm. As the % DMSO is increased the signal is reduced and indicates solubilization of the drug. We observed that >25% vol/vol DMSO is required to completely dissolve the drug at 0.2 mg/mL at a temperature of 65° C.

TABLE 3

Comparison of remote loading doxorubicin and 17-DMAG into ammonium sulfate containing liposomes in the presence and absence of 25% DMSO.

| Drug | % DMSO | % Efficiency compared to control of no DMSO |
|---|---|---|
| doxorubicin | 25 | 92.7 ± 0.43 |
| 17-DMAG | 25 | 73.1 ± 1.4 |

Conclusions

Previous studies loading carfilzomib were done using 10% v/v DMSO or less and the light scattering results above show that the vast majority of the drug under these conditions is in a precipitated form at the concentrations used. Adding enough aprotic solvent to completely solubilize the drug (i.e. greater than 25% DMSO at 65° C.) has a negative impact of the liposome loading of amphipathic weak base drugs indicating liposome instability caused by contents leakage or electrochemical gradient dissipation for example. Under conditions that maintain good liposome stability, we have not found a DMSO concentration that will solubilize carfilzomib completely or alternatively we have not found conditions using DMSO where simultaneously the drug is completely solubilized and the liposomes are not adversely destabilized.

Example 9

Effect of Delay on Liposome Loading of Carfilzomib After the Drug Precipitate is Formed Introduction The invention described in this application allows for loading of an insoluble drug precipitate into liposomes. Example 9 evaluates the effect of the time between the formation of the drug precipitate and the time it is loaded into liposomes.

Procedure

Liposomes were prepared from the same composition and methods as described in Example 1.

Carfilzomib was dissolved in DMSO at a concentration of 10 mg/mL and we added to a final concentration of 2% (v/v) to 50 mM citrate, 10% sucrose at pH 3.5 containing no liposomes. Upon addition of the drug to the citrate buffer a precipitate was formed. The liposomes for loading were added to the solution containing drug precipitate either immediately after formation, after a 1 h delay or after a 12 h delay and then the precipitate was loaded into the liposomes using the loading conditions described in Example 1.

Results/Conclusion

The time between the formation of the drug precipitate and the loading of the precipitate does not have a significant impact on the efficiency of the liposome loading procedure for carfilzomib even if the delay time is up to 12 h.

Example 10

Effect of Liposome Drug Payload on Efficiency of Carfilzomib Loaded from Precipitate Procedure Liposomes were prepared from the same composition and methods as described in *Comparison of Trapping Agents* except the concentration of ammonium sulfate internal trapping agent was either 250 mM or 500 mM.

Carfilzomib was dissolved in DMSO at a concentration of 10 mg/mL. The carfilzomib was introduced to the liposomes at carfilzomib to HSPC ratios of 91.8, 167, 251, 338 and 433, g drug/mol HSPC for the liposomes having 250 mM ammonium sulfate as the trapping agent and 451, 546, 639, and 759 g drug/mol HSPC for the liposomes having 500 mM ammonium sulfate as the trapping agent. The liposomes were diluted with 50 mM citrate, 10% sucrose pH 4.0 to increase the volume to a point where after addition of the drug the final DMSO concentration is 10%. The carfilzomib/DMSO was added to the diluted liposomes, which were mixed at room temperature then transferred to a 65° C. bath and swirled every 30 s for the first 3 min and then swirled every 5 min over a total heating time of 30 min. All samples were very cloudy when the drug was added and all became clear (same as liposomes with no drug added) after 15 min. After heating for 30 min all samples were placed on ice for 15 min. The loaded liposomes were purified and analyzed as described in Example 1.

Results/Conclusion

The resulting drug payload increases as the drug to liposome input lipid ratios is increased in the loading solution. The efficiency is greatest at the lowest input ratio used for each different concentration of ammonium sulfate trapping agent. Using the conditions described in this example, carfilzomib can be loaded into liposomes from an insoluble precipitate up to a final drug payload of 469±4.9 g drug/mol HSPC (drug/carrier total lipid weight ratio of 0.4) at an efficiency of 61.7±1.2%.

Example 11

Loading of Insoluble Carfilzomib into Liposomes Using a Triethylammonium Sulfate Gradient Introduction Remote loading of drugs into liposomes is commonly accomplished using an ammonium sulfate gradient. Some drug molecules including the example carfilzomib used here have an epoxide group which is required for activity. The epoxide of these drugs is potentially susceptible to aminolysis from any remaining ammonia that is used in the ammonium sulfate remote loading. In this, Example 11, the ammonium sulfate is replaced with a triethylammonium sulfate remote loading agent to eliminate potential ammonia/epoxide reactions by replacement with nonreactive triethylamine.

Methods

The liposomes were prepared by using the same compositions and procedure as described in *Carfilzomib Liposome Entrapment by Remote Loading* with the following exception that 50 mM triethylammonium sulfate was used as the trapping agent. Triethylammonium Sulfate was prepared by titrating 1 M sulfuric acid with triethylamine to a final pH of 7.3 and sulfate concentration of 500 mM.

Carfilzomib was dissolved in DMSO at a concentration of 10 mg/mL. The carfilzomib was introduced to the liposomes at carfilzomib to HSPC ratios of 650 g drug/mol HSPC. The liposomes were diluted with 50 mM citrate, 10% sucrose pH 4.0 to increase the volume to a point where after addition of the drug the final DMSO concentration is 10%. The carfilzomib/DMSO was added to the diluted liposomes, which were mixed at room temperature then transferred to a 65° C. bath and swirled every 30 s for the first 3 min and then swirled every 5 min. A sample of the loading mixture was removed at 10, 20, 30 and 40 min during the loading procedure and placed on ice for 15 min. The loaded lipo-

TABLE 4

Effect of Ammonium Sulfate Trapping Agent Concentration on Liposome Drug Payload of Carfilzomib Loaded from Precipitate

Figure 12:
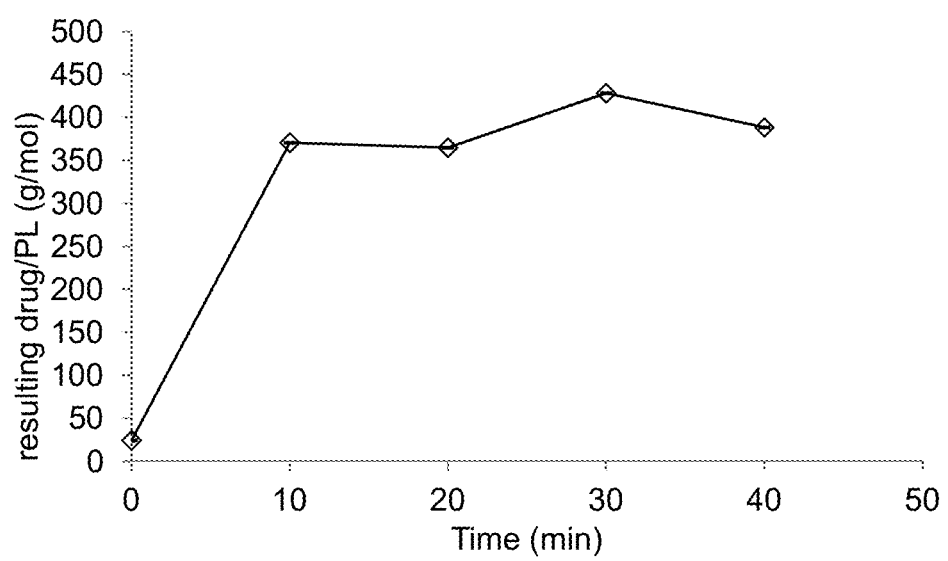
FIG. 12 is a line graph loading insoluble carfilzomib precipitate into liposomes using a triethylammonium sulfate gradient.

| Input | | | Output | | | | Drug payload/carrier weight ratio (g drug/g total lipid) |
|---|---|---|---|---|---|---|---|
| drug/HSPC (g/mol) | SD (g/mol) | trapping agent [(NH$_4$)$_2$SO$_4$] (mM) | drug/HSPC (g/mol) | SD (g/mol) | efficiency % | SD (g/mol) | |
| 91.8 | 0.3 | 250 | 83.5 | 2.7 | 90.9 | 3.0 | 0.07 |
| 167.3 | 4.2 | 250 | 127.2 | 1.5 | 76.0 | 2.1 | 0.11 |
| 251.8 | 5.8 | 250 | 174.1 | 3.9 | 69.1 | 2.2 | 0.15 |
| 338.1 | 4.1 | 250 | 210.7 | 2.5 | 62.3 | 1.1 | 0.18 |
| 432.8 | 14.4 | 250 | 240.5 | 4.4 | 55.6 | 2.1 | 0.20 |
| 450.6 | 9.6 | 500 | 345.2 | 7.1 | 76.6 | 2.3 | 0.29 |
| 545.9 | 17.1 | 500 | 380.9 | 21.4 | 69.8 | 4.5 | 0.32 |
| 639.2 | 42.5 | 500 | 438.9 | 10.2 | 68.7 | 4.8 | 0.37 |
| 758.7 | 12.4 | 500 | 468.2 | 4.9 | 61.7 | 1.2 | 0.40 | somes were vortexed and 100 μL of sample was kept as the "before column" and the rest transferred to microcentrifuge tubes and spun at 10,000 RPM for 5 min. The supernatants were purified on a Sephadex G25 column collected and analyzed by HPLC. The drug precipitate pellets were dissolved in DMSO/MeOH (10:1) and analyzed by HPLC.
Results/Conclusion Loading an insoluble carfilzomib precipitate into liposomes using a triethylammonium sulfate gradient results in similar liposomes to those produced using an ammonium sulfate gradient (Example 1). FIG. 12 illustrates the time dependence on the liposome loading, which begins quickly by 10 min. The greatest payload achieved was 440±12.6 g drug/mol HSPC (efficiency of 65.9±1.98%) was achieved at 30 min. This result using 500 mM triethylamine as a trapping agent at drug to HSPC ratios of 650 g drug/mol HSPC is very similar to that using 500 mM ammonium sulfate as the trapping agent drug to HSPC ratios of 639 g drug/mol HSPC which resulted in a final drug to lipid ratio of 440±10.2 g drug/mol HSPC (efficiency of 68.7±4.80%).

Figure 13:
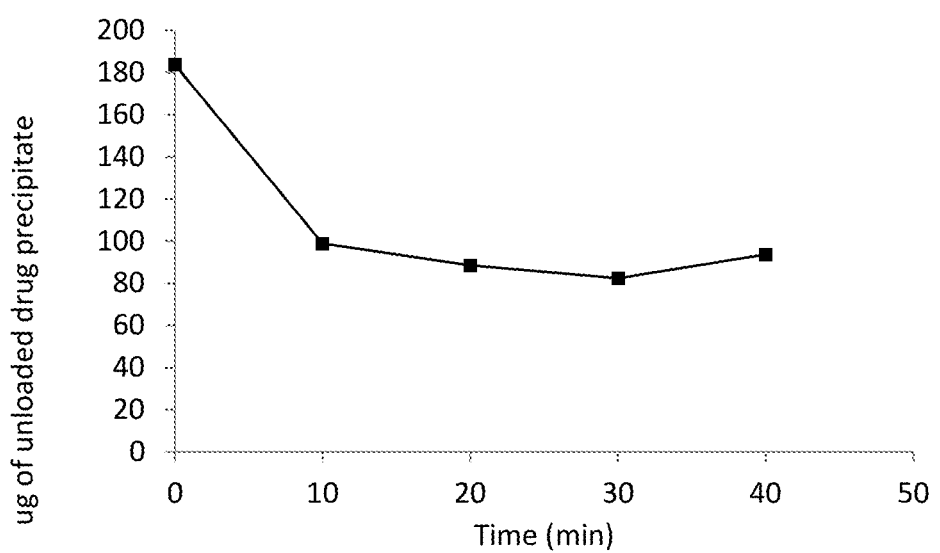
FIG. 13 is a line graph showing the transfer of insoluble carfilzomib precipitate into liposomes by remote loading.

The insoluble drug precipitate on the liposome exterior is transferred (remote loaded) to the liposome interior as indicated a reduction in the amount of precipitate in the mixture over the course of the loading process. FIG. 12 shows the greatest reduction in the extraliposomal precipitate happens between 0-10 min which corresponds to the loading of precipitate into liposomes as seen in FIG. 13.

Example 12

Loading Another Sparingly Soluble Drug from a Precipitate
Introduction

Another drug, aripiprazole is formulated with sulfobutyl cyclodextran (SBCD) and is used to treat bipolar disorders and schizophrenia (Abilify, Pfizer). The drug is very insoluble in water and when added to a liposome suspension, fine precipitates are immediately observed.

Whether aripiprazole would remote load under similar conditions outlined above for carfilzomib was tested.
Method Liposomes (HSPC/Chol/PEG-DSPE 3/2/0.15 mol/mol/mol) containing 250 mM ammonium sulfate or 250 mM sodium sulfate were diluted in 1 mL of 50 mM citric acid, 10% (wt/wt) sucrose, pH 4.0 to a concentration of 6 mM phospholipid. 0.3 mg of aripiprazole was added from a stock solution of 15 mg/mL in DMSO, so that the final DMSO concentration was 2% (v/v). Fine precipitates were immediately observed after the drug was added to both liposome samples. The samples were heated at 65° C. for 30 min, the cooled on ice. The samples were filtered through a 0.2 um polyethersulfone syringe filter to remove any drug precipitates, followed by purification on a Sephadex G25 column equilibrated with HBS, pH 6.5 to remove any soluble extraliposome drug. The turbid fraction was collected and analyzed for lipid and drug as described above.
Results

TABLE 5

Results of loading aripiprazole into liposomes containing ammonium and sodium sulfate.

| Loading Agent | Input D/L ug/umol | Output D/L ug/umol | % Efficiency | Fold Increase NH$_4$SO$_4$/NaSO$_4$ |
|---|---|---|---|---|
| (NH$_4$)$_2$SO$_4$ | 50 | 42.28 ± 0.49 | 84.56 ± 0.99 | 49.3 |
| (Na)$_2$SO$_4$ | 50 | 0.86 ± 0.51 | 1.71 ± 0.10 | |

The liposomes containing ammonium sulfate were found to load approximately 85% of the drug, while the loading into sodium sulfate liposomes was less than 2%, with about a 50-fold increase in loading attributable to the ability of ammonium sulfate liposomes to facilitate remote loading (Table 5).

Figure 14:
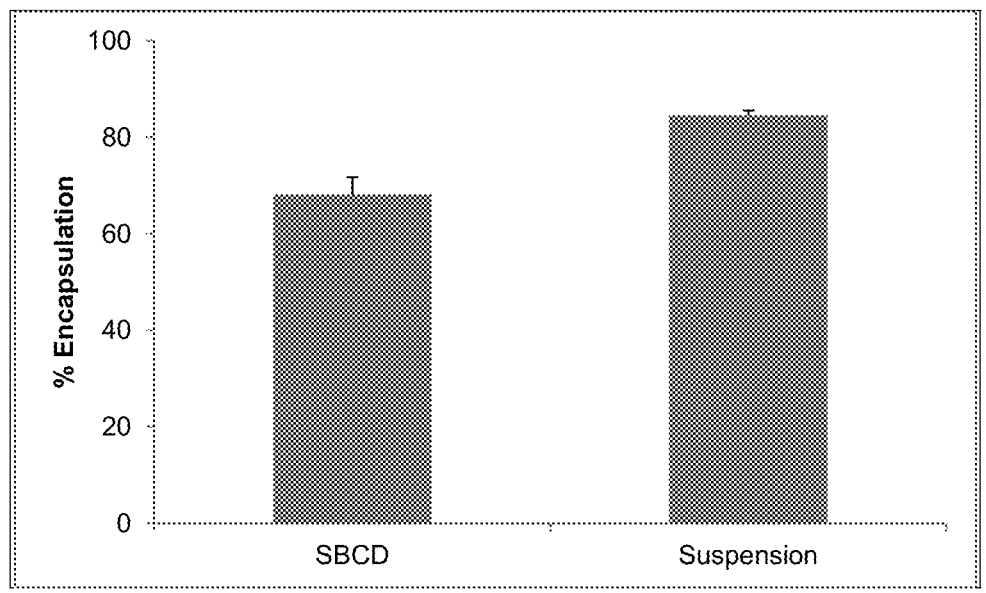
FIG. 14 is a bar graph showing the comparison of liposome loading of aripiprazole when mixed with liposomes as a SBCD complex (Abilify) or when diluted from a stock DMSO solution directly into liposomes, creating a drug suspension.

Ariprazole, when introduced to the liposome solution in the form of a SBCD complex (from the pharmaceutical product Abilify) gave a loading efficiency of 68% under the same concentration and loading conditions (FIG. 14).
Conclusion This is another example of a poorly soluble drug, that can be remote loaded into liposomes using the approach described above, and gives slightly better loading than if the drug was introduced as a SBDC complex.

Example 13

Figure 15:
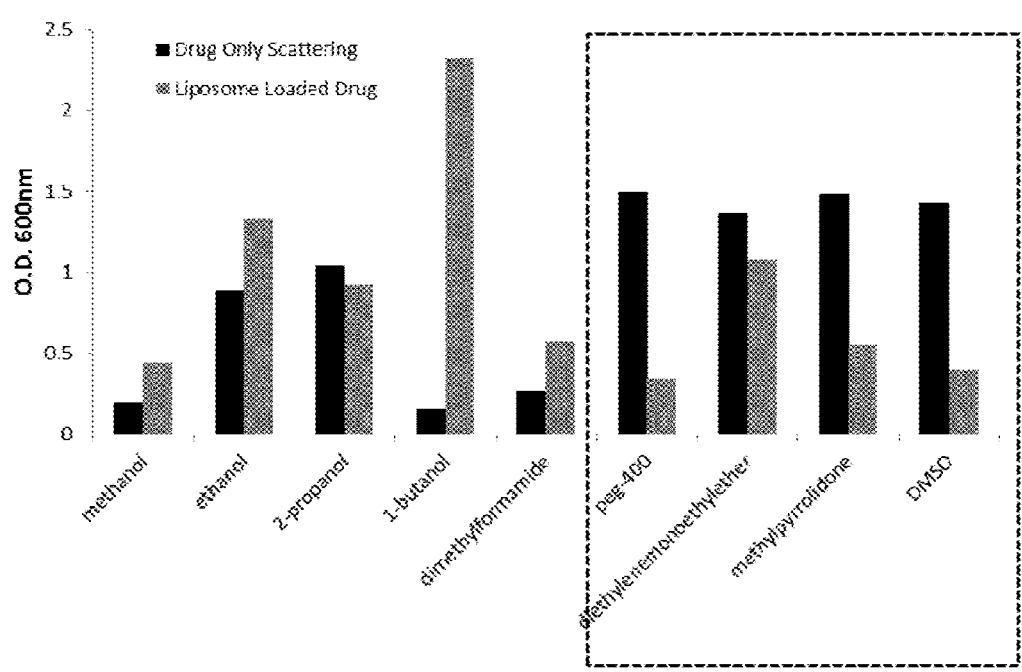
FIG. 15 is a bar graph showing absorbance at 600 nm (scattering) of drug solutions (dark bars) and liposome drug mixtures (gray bars). The rectangle indicates the samples where a substantial decrease in scattering was measured upon incubation with liposomes indicating drug loading.

Loading Sparingly Soluble Drug from Precipitates Made by Diluting Various Drug Solvent solutions into Liposome Solution This Example describes a technique for remote loading poorly soluble drugs into liposomes that begins with dissolving the drug in a solubilizing agent that initially forms drug precipitates when added to an aqueous solution of liposomes. After some incubation time the drug enters the liposome in response to an electrochemical gradient, accumulating in the liposome core. Solvents that may be used include but not limited to dimethylsulfoxide, dioxane, tetrahydrofuran, dimethylformamide, acetonitrile, dimethylacetamide, sulfolane, gamma butyrolactone, pyrrolidones, 1-methyl-2-pyrrolidinone, methylpyrroline, ethylene glycol monomethyl ether, diethylene glycol monomethyl ether, polyethylene glycol.
Method Aripiprazole was dissolved in a range of solvents indicated below at 4 mg/mL. Liposomes composed of HSPC/Chol/PEG-DSPE (3/2/0.15 mol/mol/mol) that were prepared in 250 mM ammonium sulfate were used and diluted to 6 mM in Hepes buffered sucrose 10% (wt/wt) (HBSuc pH 6.5). 0.3 mg of drug was introduced by slow addition of each solvent while vortexing. The final solvent concentration was 7.5% for all samples. As controls, the drug was added from each solvent to the same volume of HBSuc pH 6.5 without the liposomes. The samples were heated at 65° C. for 30 min then cooled on ice. After reaching room temperature again, the samples were measured for absorbance at 600 nm (Cary 100 Bio UV-Vis spectrometer) and the values are displayed below (FIG. 15).
Results All the solutions without liposomes became extremely turbid or there was gross precipitation and settling (especially in the case of methanol and 1-butanol). Some of the liposome samples were also very turbid, but some clarified the drug precipitate consistent with earlier results indicating drug loading of the drug precipitate had taken place (namely in the cases where the drug was initially dissolved in DMSO, 1-4-methylpyrrolidone, diethylenemonoethylether or polyethyleneglycol (MW400), see FIG. 15.

Example 14

Remote Loading of an Insoluble Precipitate of Deferasirox Into Liposomes Using an Acetate Gradient Remote loading of deferasirox into liposomes containing calcium acetate demonstrates the use of an acetate gradient for loading an iron chelating agent. Calcium acetate gradient remote loading differs from ammonium sulfate remote loading in that the drug molecule being loaded must have a carboxylate (or hydroxamate) rather than an amine. Deferasirox is known to have significant kidney toxicity and liposome delivery is a technique for reducing kidney toxicity.

Method

The remote loading of a deferasirox insoluble precipitate into iposomes using an acetate gradient is performed in the same manner as acetate loading of soluble carboxyfluoroscein and nalidixic acid by Clerc and Barenholtz 1995 (PMID 8541297). Liposomes are prepared as described in Example 1 but in this case the liposomes are extruded in a solution of 120 mM calcium acetate at pH 8. The acetate gradient is formed by exchanging the external media for 120 mM sodium sulfate at pH 6.0. Deferasirox is dissolved in DMSO at a concentration of 10 mg/ml and added to the liposome suspension where it forms a precipitate. The precipitate is loaded into the liposomes by heating to 65° C. for 1 h and purification and analysis is performed as described in Example 1.

Results

Deferasirox forms a precipitate when diluted from a 10 mg/ml DMSO stock to a concentration of 1 mg/ml in the liposome loading suspension due to its poor water solubility (~0.038 mg/mL). The insoluble deferasirox precipitate is loaded into the liposomes using a calcium acetate gradient at an efficiency at least 5-fold greater than it is loaded into control liposomes which contain sodium sulfate and no acetate gradient.

Remote loading an insoluble precipitate of deferasirox into the liposome provides an example of the use of an acetate gradient to remote load a carboxylate drug from a precipitate. In this example the drug being loaded is a chelating agent, in particular an iron chelating agent. The 5-fold greater loading into the liposomes having an acetate gradient over control liposomes indicates that the majority of the deferasirox is remote loaded rather than intercalated in the lipid bilayer.

Example 15

Introduction

One goal of liposomal delivery of carfilzomib is to protect the drug from degradation and elimination which required the drug to be retained within the liposome. One technique for evaluating the drug retention within the liposome, and thus the benefits obtained from liposome delivery, is to measure the pharmacokinetics of the drug in mice. Stable formulations with greater drug retention within the liposome will result in a higher concentration of non-metabolized drug in mouse plasma compared to less stable formulations or unencapsulated drug.

Materials and Methods 100 nm liposomes comprised of HSPC/Cholesterol/PEG-DSPE (60/40/5 mol/mol/mol) and sphingomyelin/cholesterol/PEG-DSPE (55/45/2.8, mol/mol/mol) were formed, purified and drug loaded with carfilzomib using the methods described in Example 1. The trapping agents used to remote load carfilzomib were triethylammonium dextran sulfate (1.0 M $SO_4$) or triethylammonium sucroseoctasulfate (1.0 M $SO_4$). The drug loaded liposomes were purified by tangential flow filtration with buffer exchange into HBS, pH 6.5. The liposomes were sterile filtered through 0.2 um polyethersulfone filters and assayed for carfilzomib and lipid content as described in Example 1. The drug-to-lipid ratio, drug concentration and loading efficiency were calculated and results shown in Table 6.

Results.

TABLE 6

Carfilzomib concentration in mouse plasma after IV. administration of liposome formulations.

| # | Lipid Formulation (mol/mol/mol) | Trapping Agent | Drug Loading Efficiency | CFZ/PL (µg/µmol) | % ID @ 4 h |
|---|---|---|---|---|---|
| 1 | HSPC/Chol/PEG-DSPE (60/40/5) | Ammonium Sucrose Octasulfate (1.0M $SO_4$) | 94.1 ± 0.43 | 329.2 ± 2.26 | 0.65 ± 0.29 |
| 2 | HSPC/Chol/PEG-DSPE (60/40/5) | Triethylammonium Dextran Sulfate (1.0M $SO_4$) | 94.6 ± 7.55 | 381 ± 12.1 | 4.48 ± 1.10 |
| 3 | HSPC/Chol/PEG-DSPE (60/40/5) | Triethylammonium Dextran Sulfate (1.0M $SO_4$) | 94.6 ± 7.55 | 381 ± 12.1 | 5.53 ± 1.69† |
| 4 | SM/Chol/PEG-DSPE (55/45/2.8) | Triethylammonium Dextran Sulfate (1.0M $SO_4$) | 80.4 ± 0.71 | 321.8 ± 7.98 | 66.3 ± 20.3 |

†formulation #3 is the same as #2 except it was stored at 4° C. for 30 days before PK analysis In addition, we examined the pharmacokinetics of carfilzomib encapsulated in the liposome formulations in male CD1 mice. The mice were dosed by IV bolus injection through the tail vein at 5 mg/kg carfilzomib using 3 mice per formulation. At 4 h, the mice were sacrificed and plasma harvested by centrifugation of the blood. 0.1 mL of plasma was mixed with 0.2 mL methanol, mixed well and carfilzomib concentration measured by HPLC as described in Example 1. The loading efficiency, drug/lipid ratio and percent of the injected dose remaining in the plasma 4 hours after a tail vein injection of the liposome carfilzomib (% ID@ 4 h) are shown in Table 6. While no effort was made to distinguish between non-liposome entrapped and liposome entrapped drug in the plasma as our analysis measures total drug content we presume that the majority of the measured carfilzomib is liposome entrapped because the drug is very rapidly eliminated in the blood stream ($t_{1/2}$<20 min) (Yang et al 2011, Drug Metab Dispos. 2011 October; 39(10):1873-82). We observed a 100-fold range of drug retention from 0.65% to 66.3% ID depending on the liposome formulation composition. The most stable liposome tested was sphingomyelin based and contained an internal ammonium dextran sulfate solution. The liposomes described above increased the plasma retention of carfilzomib 46-to-4735 fold more than a SBCD formulation, or 5-to-510 fold higher than published liposome formulations at 4 h post administration. (Chu et al 2012 AAPS Meeting, Poster T2082).

Example 16

Figure 16:
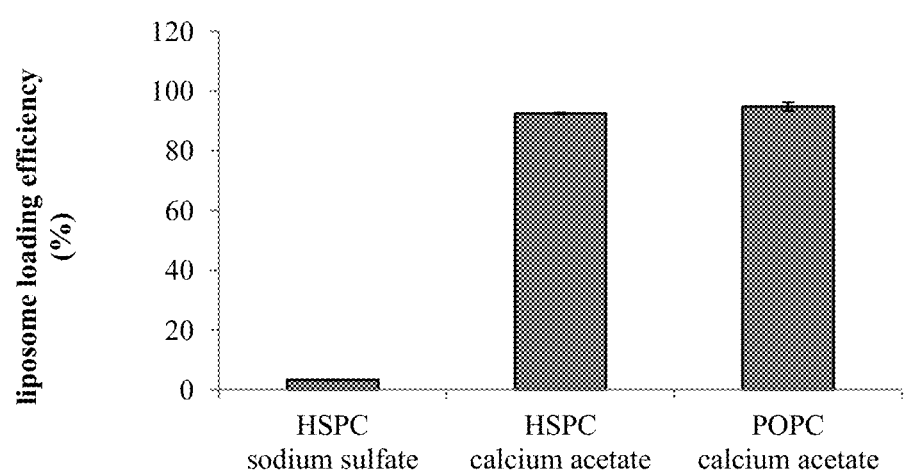
FIG. 16 is a bar graph showing the loading efficiency of DFX in calcium acetate liposomes.

Remote Loading of an Insoluble Precipitate of Deferasirox Into Liposomes Using an Acetate Gradient
Introduction Remote loading of deferasirox (DFX) into liposomes containing calcium acetate demonstrates the use of an acetate gradient for loading an iron chelating agent. Calcium acetate gradient remote loading differs from ammonium sulfate remote loading in that the drug molecule being loaded must have a carboxylate (or hydroxamate) rather than an amine. Deferasirox is known to have significant kidney toxicity and liposome delivery is a technique for reducing kidney toxicity.
Method Liposomes were prepared using the extrusion and purification method described in Example 1. The lipid composition was HSPC/Cholesterol (3/0.5, mol/mol) or POPC/cholesterol (3/0.5, mol/mol). The trapping agent consisted of calcium acetate or sodium sulfate each at a concentration of 120 mM. A solution of DFX in DMSO at 20 mg/mL was added to the liposome solution slowly over 30 seconds while vortexing to produce a drug precipitate in the liposome solution. The target drug to phospholipid ratio was 100 g DFX/mol phospholipid. The solution was heated for 30 min (at 45° C. for POPC liposomes and 65° C. for HSPC liposomes) and then cooled on ice. A sample was removed to determine the input drug to lipid ratio and the remaining solution was spun in a centrifuge at 12,000 RPM for 5 minutes to pellet any unloaded drug. The supernatant was further purified from unloaded drug using a Sephadex G25 size exclusion column eluted with 5 mM HEPES, 145 mM NaCl at pH 6.5. The purified liposomes are analyzed for drug and lipid content by HPLC using the system described in Example 1 and a program consisting of gradient elution of 65% B to 98% B in 6 min with 5 min equilibration back to 65% B (A=0.1% TFA, B=0.1% TFA/MeOH, 1.0 mL/min), column temperature held constant at 30° C., 10 ul injection, and detection by absorbance at 254 nm.
Results Upon addition of the drug in DMSO to the liposomes containing calcium acetate as the trapping agent, the solution of POPC liposomes were less cloudy than the solution of HSPC liposomes, both contained precipitated drug before loading. After heating, the solutions clarified and appeared like liposomes with no drug precipitate. Liposomes containing sodium sulfate as the control trapping agent never clarified during the heating process and a drug precipitate pellet was formed upon centrifugation. The loading of liposomes containing calcium acetate made from POPC and HSPC was very efficient. Both liposomes containing the calcium acetate trapping resulted in >90% loading efficiency. The liposomes containing sodium sulfate resulted in 3.3% loading efficiency, which indicates that the loading of DFX into calcium acetate liposomes is not passive but can be described as remote loading. The DFX loading results are shown in Table 7 (FIG. 16).

TABLE 7

Loading Efficiency of DFX in Calcium Acetate Liposomes 2

| Lipid composition | Interior buffer | DFX loading efficiency |
|---|---|---|
| 3 mol POPC/0.5 mol Chol | 120 mM calcium acetate | 94.8 ± 1.46% |
| 3 mol HSPC/0.5 mol Chol | 120 mM calcium acetate | 92.5 ± 0.33% |
| 3 mol HSPC/0.5 mol Chol | 120 mM sodium sulfate | 3.3 ± 0.14% |

Conclusion

Remote loading an insoluble precipitate of deferasirox into the liposome provides an example of the use of an acetate gradient to remote load a carboxylate drug from a precipitate. In this example the drug loaded was a chelating agent, in particular an iron chelating agent. The 28-fold greater loading into the liposomes having an acetate gradient over control liposomes indicates that the majority of the deferasirox is remote loaded rather than intercalated in the lipid bilayer.

Example 17

Figure 17:
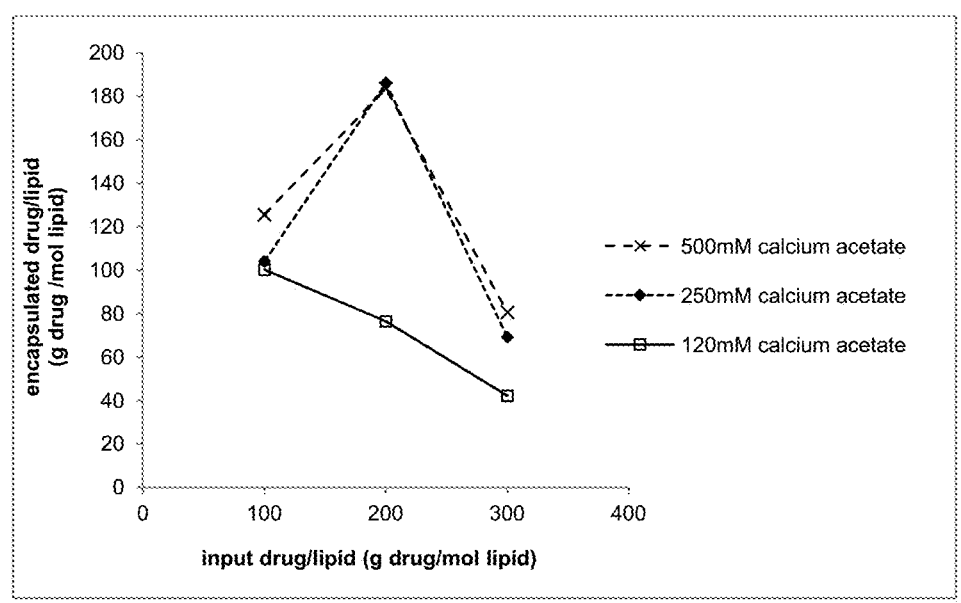
FIG. 17 is a plot showing DFX loading capacity in liposomes containing calcium acetate as a trapping agent.

Remote Loading of an Insoluble Precipitate of Deferasirox Into Liposomes. Evaluation of Drug to Lipid Ratio and Calcium Acetate Trapping Agent Concentration.
Introduction The remote loading capacity of DFX in liposomes containing calcium acetate was evaluated by using different concentrations calcium acetate on the liposome interior and loading a range of different DFX-to-lipid ratios.
Method Liposomes were prepared using the extrusion and purification method described in Example 1. The lipid composition was POPC/cholesterol (3/0.5, mol/mol). The trapping agent consisted of calcium acetate 120 mM, 250 mM or 500 mM. A solution of DFX in DMSO at 20 mg/mL was added to the liposome solution slowly over 30 seconds while vortexing to produce a drug precipitate in the liposome solution. The target drug to phospholipid ratio was 100, 200 or 300 g DFX/mol phospholipid. The solution was heated for 30 min at 45° C. and then cooled on ice. A sample was removed to determine the input drug to lipid ratio and the remaining solution was spun in a centrifuge at 12,000 RPM for 5 minutes to pellet any unloaded drug. The supernatant was further purified from unloaded drug using a Sephadex G25 size exclusion column eluted with 5 mM HEPES, 145 mM NaCl at pH 6.5. The purified liposomes are analyzed for drug and lipid content by HPLC as described in Example 16.
Results Upon addition of the drug in DMSO to the liposomes containing calcium acetate as the trapping agent the DFX forms a precipitate before loading. After heating, the solutions clarify and look like liposomes with no drug precipitate. The maximum drug load was higher for liposomes containing 250 and 500 mM calcium acetate compared to 120 mM calcium acetate. The maximum drug load and efficiency was achieved at an input of 200 g DFX/mol phospholipid for liposomes containing either 250 mM calcium acetate or 500 mM calcium acetate. The efficiency of loading for a target of 100 g DFX/mol phospholipid ranged from 99.2 to 103% for all three concentrations of internal calcium acetate. When the target drug load was increased to 200 g DFX/mol phospholipid the efficiency of liposomes having 250 or 500 mM internal calcium acetate was at least two-fold greater than liposomes having an internal calcium acetate concentration of 120 mM. The capacity of all three liposomes was exceeded at input of 300 g DFX/mol phospholipid resulting in n efficiency <24%. The results are shown in FIG. 17.

Conclusion

The drug payload capacity of DFX when remote loaded into liposomes can be substantially increased by increasing the concentration of the trapping agent concentration inside the liposome. This example demonstrates the dependence of loading capacity on calcium acetate trapping agent concentration. This example also demonstrates DFX liposome loading can have an optimum drug to lipid ratio where the efficiency and drug load are both greatest. The achieved drug to lipid ratio allows for the DFX to be administered to an animal using a tolerated dose of lipid.

Example 18

Remote Loading of an Insoluble Precipitate of Deferasirox Into Liposomes. Evaluation of Trapping Agent.

The remote loading capacity of DFX in liposomes containing calcium acetate, magnesium acetate and zinc acetate was evaluated by preparing liposomes with different trapping agents on the interior and loading a range of different DFX-to-lipid ratios.

Method

Liposomes were prepared using the extrusion and purification method described in Example 1. The lipid composition was POPC/cholesterol (3/0.5, mol/mol). The trapping agent consisted of calcium acetate, magnesium acetate or zinc acetate at 120 mM. A solution of DFX in DMSO at 20 mg/mL was added to the liposome solution slowly over 30 seconds while vortexing to produce a drug precipitate in the liposome solution. The target drug to phospholipid ratio was 100, 150 or 200 g DFX/mol phospholipid. The solution was heated for 30 min at 45° C. and then cooled on ice. A sample was removed to determine the input drug to lipid ratio and the remaining solution was spun in a centrifuge at 12,000 RPM for 5 minutes to pellet any unloaded drug. The supernatant was further purified from unloaded drug using a Sephadex G25 size exclusion column eluted with 5 mM HEPES, 145 mM NaCl at pH 6.5. The purified liposomes are analyzed for drug and lipid content by HPLC as described in Example 16.

Results

Figure 18:
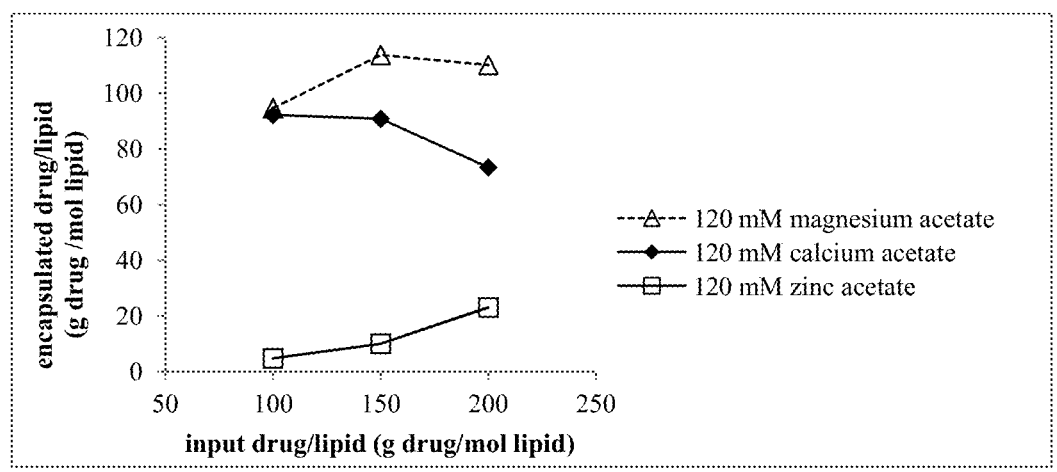
FIG. 18 is a plot showing DFX loading capacity in liposomes containing different acetate trapping agents.

Upon addition of the drug in DMSO to the liposomes, the DFX forms a precipitate before loading. After heating, the solutions containing liposomes with calcium acetate and magnesium acetate became much less turbid than the liposomes containing zinc acetate as the trapping agent. The maximum drug load was highest for the liposomes containing magnesium the second highest for the liposomes containing calcium acetate and the liposomes containing zinc acetate resulted in the lowest drug payload. The efficiency of loading for a target of 100 g DFX/mol phospholipid was 5.3±0.07% using zinc acetate whereas the efficiency using calcium acetate and or magnesium acetate were 97.6±0.41% and 99.2±2.42%, respectively. The results are shown in FIG. 18.

Conclusion

The drug payload capacity of DFX when remote loaded into liposomes can be dependent on the particular metal salt of acetate used for remote loading. This example demonstrates that magnesium acetate is a better trapping agent for DFX than calcium acetate or zinc acetate, and both are far superior trapping agents than zinc acetate.

Example 19

Introduction

The loading agent and liposome composition influences how effectively liposome formulations containing carfilzomib can be prepared and the liposomes' in vivo pharmacokinetic properties.

Materials and Methods 100 nm liposomes comprised of HSPC/Cholesterol/PEG-DSPE (60/40/5 mol/mol/mol) and sphingomyelin/cholesterol/PEG-DSPE (55/45/2.8, mol/mol/mol) were formed, purified and drug loaded with carfilzomib using the methods described in Example 1. The trapping agents used to remote load carfilzomib were 0.65 M citric acid, 0.65 triethylammonium citrate, 0.33 M triethylammonium mellitic acetate, and triethylammonium napthalene disulfate (1.0 M $SO_4$). The drug loaded liposomes were purified by dialysis with buffer exchange into HBS, pH 6.5. The liposomes were sterile filtered through 0.2 um polyethersulfone filters and assayed for carfilzomib and lipid content as described in Example 1. The drug-to-lipid ratio, loading efficiency and percent injected dose remaining in plasma 4 h after a tail injection into a mouse (% ID @ 4 h) were calculated and results shown in Table 8.

Results.

TABLE 8

Carfilzomib liposome loading results and concentration in mouse plasma after IV administration of liposome formulations.

| # | Lipid Formulation (mol/mol/mol) | Trapping Agent | Drug Loading Efficiency (%) | CFZ/PL (µg/µmol) | % ID @ 4 h |
|---|---|---|---|---|---|
| 1 | HSPC/Chol/PEG-DSPE (60/40/5) | 0.65M Citric acid | Sample aggregates | N.D. | N.D. |
| 2 | HSPC/Chol/PEG-DSPE (60/40/5) | 0.65M triethylammonium citrate | Sample aggregates | N.D. | N.D. |
| 3 | HSPC/Chol/PEG-DSPE (60/40/5) | 0.33M triethylammonium mellitic acetate | Sample aggregates | N.D. | N.D. |
| 4 | HSPC/Chol/PEG-DSPE (60/40/5) | Naphthalene disulfate (1.0M $SO_4$) | 85.7 ± 4.67 | 300 ± 16.3 | non detectable |

N.D. = not done because the samples aggregated

Upon addition of the drug in DMSO to the liposomes, the carfilzomib forms a precipitate before loading. After heating, formulations 1-3 in Table 8 showed an increase in turbidity due to large aggregates in the remote loading mixture that did not allow for purification of the liposomes. Formulation 4 of Table 8 became less turbid after heating and resulted in a loading efficiency of 85.7±4.67%. Formulation 4 of Table 8 was evaluated for drug retention in plasma four hours after IV injection in mice. At four hours post injection, there was no detectable carfilzomib present in the plasma. This is to be contrasted to the results in table 6 where all four formulations had measureable and significant quantities of carfilzomib in plasma at four hours post-injection.

Conclusion

From inspection of the data in Table 6 and 8 it is clear that optimization of liposome formulation for retention of carfilzomib in plasma after intravenous injection in mice requires: precise control of the liposome composition and the encapsulation of the appropriate remote loading agent. Formulations based upon the widely used FDA approved Doxil® product were inferior to the optimal lipid composition of SM/Chol/PEG-DSPE (55/45/2.8). The amine salt of dextran sulfate was encapsulated.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

All publications, patents, and patent applications cited herein are hereby incorporated by reference in their entirety for all purposes.

What is claimed is:

1. A method of remotely loading a solid sparingly water-soluble active agent into liposomes from an aqueous suspension comprising the solid sparingly soluble active agent, said method comprising:
    (a) preparing a suspension of the liposomes in an aqueous medium having a proton or an ion gradient across the liposome membrane;
    (b) preparing a solution of the sparingly water-soluble agent by completely dissolving said sparingly water-soluble agent in a solvent selected from an aprotic solvent and a polyol;
    (c) forming a loading suspension comprising said solid sparingly water-soluble agent by contacting the liposome suspension in (a) with the solution of the sparingly water-soluble agent in (b), thereby diluting (b) beyond the point of the agent's solubility, precipitating the sparingly water-soluble active agent into the aqueous medium, thereby forming the loading suspension comprising the solid sparingly water-soluble agent and the liposomes, wherein said loading suspension scatters light more than said suspension of liposomes; and
    (d) incubating the final suspension of (c) for a period of time sufficient for the solid sparingly water-soluble agent to be remotely loaded from the aqueous medium into the liposomes by the proton or ion gradient.

2. The method according to claim 1, wherein at least about 70% of the solid sparingly water-soluble active agent in, the loading suspension is remotely loaded into the liposome.

3. The method according to claim 1, wherein the liposomes have a size of from about 30 nanometers to about 40 microns.

4. The method according to claim 1, wherein the liposomes comprise from about 50 mol % to about 70 mol % HSPC, from about 25 mole % to about 50 mole % cholesterol and from about 0 mol % to about 10 mol % PEG-DSPE.

5. The method according to claim 4, wherein the liposomes comprise about 60 mol % HSPC, about 40 mol % cholesterol and about 5 mol % PEG-DSPE.

6. The method according to claim 1, wherein the liposomes comprise from about 45 mole % to about 75 mole % sphingomyelin, from about 25 mole % to about 50 mole % cholesterol and from about 0 mole % to about 10 mole % PEG-DSPE.

7. The method according to claim 6, wherein the liposomes comprise about 55 mole % sphingomyelin, about 45 mole % cholesterol and about 2.8 mole % PEG-DSPE.

8. The method according to claim 1, wherein the sparingly water-soluble active agent has an aqueous solubility of less than 2 mg/mL.

9. The method according to claim 6, wherein the sparingly water-soluble active agent has an aqueous solubility at pH 7 of less than 2 mg/mL.

10. The method according to claim 1, wherein the gradient is a gradient of a member selected from an amine or a metal salt of a member selected from a carboxylate, a sulfate, a sulfonate, a phosphate a phosphonate and an acetate.

11. The method according to claim 8, wherein the gradient is a gradient of a member selected from ammonium sulfate, triethylammonium sulfate, calcium acetate magnesium acetate, and ammonium chloride.

12. The method according to claim 1, wherein the gradient is a gradient of triethylammonium dextran sulfate or ammonium dextran, sulfate.

13. The method according to claim 1, wherein the loading efficiency (grams encapsulated agent/moles of phospholipid) is at least 90% of the active agent precipitate.

14. The method according to claim 1, wherein the sparingly water-soluble active agent is carfilzomib and about 60 mg of the carfilzomib is loaded into from about 90 mg to about 200 mg of lipid.

15. The method according to claim 12, wherein about 60 mg of carfilzomib is loaded into about 170 mg of lipid.

16. The method according to claim 12, wherein the liposomes are from about 40 nm to about 150 nm in diameter.

17. The method according to claim 1, further comprising, following (c), isolating said liposomes and suspending them in a pharmaceutically acceptable carrier.

* * * * *